United States Patent [19]

Hiratsuka et al.

[11] Patent Number: 5,232,897

[45] Date of Patent: Aug. 3, 1993

[54] HERBICIDAL PYRIMIDINE COMPOUNDS, COMPOSITIONS CONTAINING THE SAME AND METHOD OF USE

[75] Inventors: Mitsunori Hiratsuka, Toyonaka; Naonori Hirata, Sanda; Kazuo Saitoh; Hideyuki Shibata, both of Toyonaka, all of Japan

[73] Assignee: Sumitomo Chemical Company, Limited, Osaka, Japan

[21] Appl. No.: 970,249

[22] Filed: Nov. 2, 1992

Related U.S. Application Data

[63] Continuation of Ser. No. 782,547, Oct. 25, 1992, abandoned, which is a continuation-in-part of Ser. No. 699,392, May 14, 1991, abandoned.

[30] Foreign Application Priority Data

May 15, 1990 [JP] Japan ................................. 2-126454
Apr. 25, 1991 [JP] Japan ................................. 3-125494

[51] Int. Cl.$^5$ ............... A01N 43/54; C07D 405/12; C07D 405/14; C07D 319/06
[52] U.S. Cl. .......................... 504/239; 504/242; 504/243; 544/299; 544/300; 544/301; 544/302; 544/303; 544/304; 544/309; 544/310; 544/312; 544/314; 544/316; 544/318; 546/268; 546/283; 546/301; 546/302; 549/346; 549/347; 549/372; 549/420; 549/449; 549/475; 549/510; 549/511; 549/555; 549/561
[58] Field of Search ............... 544/299, 300, 301, 302, 544/309, 310, 312, 313, 314, 318; 504/239, 242, 243

[56] References Cited

U.S. PATENT DOCUMENTS

| | | | |
|---|---|---|---|
| 4,248,619 | 2/1981 | Serban et al. | 71/92 |
| 4,624,802 | 11/1986 | Schaper et al. | 512/21 |
| 4,871,387 | 10/1989 | Sasse et al. | 544/302 |
| 4,889,552 | 12/1989 | Wada et al. | 544/299 |
| 4,973,354 | 11/1990 | Hatanaka et al. | 71/92 |
| 5,006,155 | 4/1991 | Rheinheimer et al. | 71/92 |
| 5,015,285 | 5/1991 | Rheinheimer et al. | 71/92 |
| 5,057,143 | 10/1991 | Rheinheimer et al. | 544/300 |
| 5,125,957 | 6/1992 | Hiratsuka et al. | 71/92 |
| 5,129,938 | 7/1992 | Hiratsuka et al. | 71/92 |
| 5,135,563 | 8/1992 | Hiratsuka et al. | 71/92 |

FOREIGN PATENT DOCUMENTS

| | | |
|---|---|---|
| 39549 | 6/1989 | Australia . |
| 0223406 | 5/1987 | European Pat. Off. . |
| 0249707 | 12/1987 | European Pat. Off. . |
| 0249708 | 12/1987 | European Pat. Off. . |
| 0287072 | 10/1988 | European Pat. Off. . |
| 0287079 | 10/1988 | European Pat. Off. . |
| 0314623 | 5/1989 | European Pat. Off. . |
| 0315889 | 5/1989 | European Pat. Off. . |
| 0321846 | 6/1989 | European Pat. Off. . |

(List continued on next page.)

OTHER PUBLICATIONS

Masato et al. Chemical Abstracts, vol. 104, 1986, p. 627, abstract No. 139395s, Columbus, Ohio, US; & JP-A-60 198 289 (Fuji Film) Jul. 10, 1985.

(List continued on next page.)

*Primary Examiner*—Emily Bernhardt
*Attorney, Agent, or Firm*—Stevens, Davis, Miller & Mosher

[57] ABSTRACT

Herbicidal pyrimidine compound having the formula

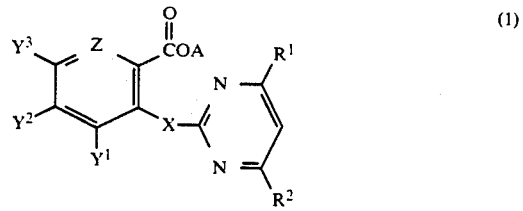

(1)

wherein the substitutents A, $R^1$, $R^2$, X, $Y^1$, $Y^2$, $Y^3$ and Z are as defined herein below.

17 Claims, No Drawings

FOREIGN PATENT DOCUMENTS

| | | |
|---|---|---|
| 0335409 | 10/1989 | European Pat. Off. |
| 0336494 | 10/1989 | European Pat. Off. |
| 0346789 | 12/1989 | European Pat. Off. |
| 0360163 | 3/1990 | European Pat. Off. |
| 0372329 | 6/1990 | European Pat. Off. |
| 0374839 | 6/1990 | European Pat. Off. |
| 0402751 | 12/1990 | European Pat. Off. |
| 3400342 | 7/1985 | Fed. Rep. of Germany |
| 3910635 | 10/1990 | Fed. Rep. of Germany |
| 3927382 | 2/1991 | Fed. Rep. of Germany |
| 54-117486 | 9/1979 | Japan |
| 63-258462 | 10/1988 | Japan |
| 63-258463 | 10/1988 | Japan |
| 63-258467 | 10/1988 | Japan |
| 1290671 | 11/1989 | Japan |
| 2-56469 | 2/1990 | Japan |
| 3-31266 | 2/1991 | Japan |
| 3-52873 | 3/1991 | Japan |
| 3128362 | 5/1991 | Japan |
| 2237570 | 5/1991 | United Kingdom |

OTHER PUBLICATIONS

Derwent Abstract for DE3927382 (Feb. 21, 1991).
Derwent Abstract for EP402751 (Dec. 19, 1990).
Derwent Abstract for JP63-258467 (Oct. 25, 1988).
Derwent Abstract for JP63-258463 (Oct. 25, 1988).
Chemical Abstracts, vol. 110, No. 130532 for JP 63-258467 (Oct. 25, 1988).
Chemical Abstracts, vol. 110, No. 192853 for JP 63-258463 (Oct. 25, 1988.
Derwent Abstract for JP63-258462 (Oct. 1988).
Chemical Abstract vol. 110, No. 192854 for JP63-258462 (Oct. 1988).
Derwent Abstract for JP1-290671 (Nov. 1989).
Derwent Abstract for JP2-56469 (Feb. 1990).
Derwent Abstract for JP54-117486 (Sep. 1979).
Derwent Abstract for DE3910635 (Oct. 1990).
Abstract for JP3-52873 (Mar. 1991).
Abstract for JP3-31266 (Feb. 1991).

HERBICIDAL PYRIMIDINE COMPOUNDS, COMPOSITIONS CONTAINING THE SAME AND METHOD OF USE

CROSS-REFERENCE TO RELATED APPLICATIONS

This application is a continuation of application Ser. No. 07/782,547, filed Oct. 25, 1992, now abandoned, which in turn is a continuation-in-part of application Ser. No. 07/699,392, filed May 14, 1991, now abandoned.

The present invention relates to a novel pyrimidine derivative, a method for producing the same, its use as a herbicide and an intermediate of the same.

European Patent Application No. 0223 406Al, 0249 708Al, 0249 707Al, etc. disclose that pyrimidine derivatives can be used as an active ingredient for herbicides.

However, these compounds are not always said to be satisfactory because they are insufficient in herbicidal activity.

On the other hand, a large number of herbicides for crop lands or non-crop lands are now in use. However, there are many kinds of weeds to be controlled and generation of the weeds extends over a long period of time, so that development of herbicides having a higher herbicidal activity and a broader herbicidal spectrum than before is being desired Further, in recent years, no-till cultivation has been carried out for the purposes of saving labor, extending cultivation period, preventing soil erosion, etc. Therefore, it is being much desired to develop herbicides having both a high post-emergence herbicidal activity against weeds and pre-emergence herbicidal activity, their excellent residual activity at high level, and a high selectivity to the undesired weeds as compared with the desired crops when crops are cultivated after application of herbicides.

In view of the situation like this, the present inventors have extensively studied, and as a result, have found that pyrimidine derivatives represented by the following formula (1) are compounds having an excellent herbicidal activity and having few foregoing defects, and that some of the derivatives have a high selectivity to the undesired weeds as compared with the desired crops. That is, the pyrimidine derivative can control the undesired weeds widely generated in crop lands or non-crop lands at low dosage rates, has a broad herbicidal spectrum and also can safely be used for no-till cultivation. The present invention is based on this finding.

According to the present invention, there are provided a pyrimidine derivative having the formula (hereinafter present compound),

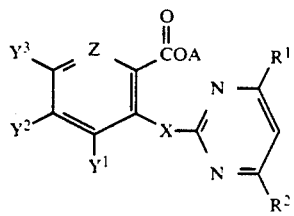
(1)

wherein A is $C_3$-$C_6$ oxacycloalkyl, $C_3$-$C_6$ oxacycloalkyl substituted with at least one member selected from the group consisting of $C_1$-$C_6$ alkyl, and halogen, $C_2$-$C_6$ oxacycloalkyl $C_1$-$C_6$ alkyl, $C_2$-$C_6$ oxacycloalkyl $C_1$-$C_6$ alkyl substituted with at least one member selected from the group consisting of $C_1$-$C_6$ alkyl and halogen, $C_3$-$C_5$ dioxacycloalkyl, $C_3$-$C_6$ dioxacycloalkyl substituted with at least one member selected from the group consisting of $C_1$-$C_6$ alkyl and halogen, $C_3$-$C_5$ dioxacycloalkyl $C_1$-$C_6$ alkyl or $C_3$-$C_5$ dioxacycloalkyl $C_1$-$C_6$ alkyl substituted with at least one member selected from the group consisting of $C_1$-$C_6$ alkyl and halogen;

each of $R^1$ and $R^2$, which may be the same or different, is $C_1$-$C^6$ alkyl, $C_1$-$C^6$ alkoxy, halo $C_1$-$C^6$ alkoxy or halogen;

X is oxygen or sulfur;

Z is nitrogen or $CY^4$;

each of $Y^1$, $Y^2$ and $Y^3$, which may be the same or different, is hydrogen, halogen, $C_1$-$C^6$ alkyl or $C_1$-$C^6$ alkoxy; and $Y^4$ is hydrogen, hydroxyl, mercapto, nitro, halogen, $C_1$-$C_6$ alkyl, $C_2$-$C_6$ alkenyl, $C_2$-$C_6$ alkynyl, $C_1$-$C_6$ alkoxy, $C_3$-$C_6$ alkenyloxy, $C_3$-$C_6$ alkynyloxy, halo $C_1$-$C_6$ alkyl, halo $C_2$-$C_6$ alkenyl, halo $C_2$-$C_6$ alkynyl, halo $C_1$-$C_6$ alkoxy, halo $C_3$-$C_6$ alkenyloxy, halo $C_3$-$C_6$ alkynyloxy, $C_1$-$C_6$ alkoxy $C_1$-$C_6$ alkyl, $C_3$-$C_6$ alkenyloxy $C_1$-$C_6$ alkyl, $C_3$-$C_6$ alkynyloxy $C_1$-$C_6$ alkyl, cyano, formyl, carboxyl, $C_1$-$C_6$ alkoxycarbonyl, $C_3$-$C_6$ alkenyloxycarbonyl, $C_3$-$C_6$ alkynyloxycarbonyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenoxy, phenoxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenylthio, phenylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzyloxy, benzyloxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzylthio, benzylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen,

wherein each of $R^5$ and $R^6$, which may be the same or different, is hydrogen, $C_1$-$C_6$ alkyl, $C_3$-$C_6$ alkenyl or $C_3$-$C_6$ alkynyl,

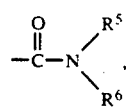

wherein $R^5$ and $R^6$ are as defined above,

wherein $R^7$ is $C_1$-$C_6$ alkyl, $C_3$-$C_6$ alkenyl or $C_3$-$C_6$ alkynyl and m is an integer of 0, 1 or 2,

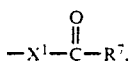

wherein $X^1$ is oxygen or sulfur, and $R^7$ is as defined above, or

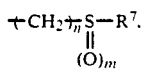

wherein $R^7$ and m are as defined above, and n is an integer of from 1 to 4; a method for producing the pyrimidine derivative (1) which comprises reacting a compound having the formula,

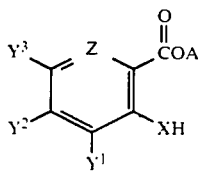

(2)

wherein A, X, Z, $Y^1$, $Y^2$ and $Y^3$ are as defined above, with a compound having the formula,

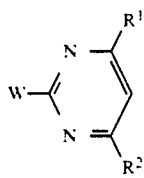

(3)

wherein each of $R^1$ and $R^2$ are as defined above; W is halogen or

wherein $R^8$ is $C_1$–$C_6$ alkyl, benzyl or benzyl substituted with at least one member selected from the group consisting of $C_1$–$C_6$ alkyl, $C_1$–$C_6$ alkoxy, halogen or nitro; and l is an integer of 0, 1 or 2; a method for producing the pyrimidine derivative (1) which comprises the steps of (i) reacting a carboxylic acid derivative having the formula (4),

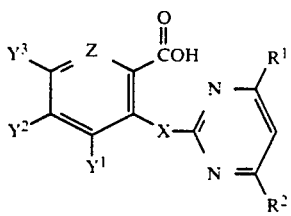

(4)

wherein X, Z, $Y^1$, $Y^2$, $Y^3$, $R^1$ and $R^2$ are as defined above, with an acid-halogenating agent or an active esterifying agent to obtain a reaction product; and (ii) reacting the reaction product with an alcohol derivative having the formula,

HO—A (5)

wherein A is a defined above; a method for producing the pyrimidine derivative (1) which comprises reacting a carboxylic acid derivative having the formula (4),

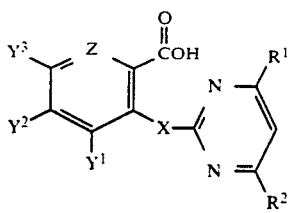

(4)

wherein X, Z, $Y^1$, $Y^2$, $Y^3$, $R^1$ and $R^2$ are as defined above, with a halide having the formula, $W^3$—A (7)

wherein A is as defined above, and $W^3$ is halogen; a compound having the formula,

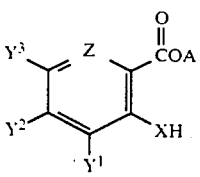

(2)

wherein A, X, Z, $Y^1$, $Y^2$ and $Y^3$ are as defined above; a herbicidal composition which comprises as an active ingredient a herbicidally effective amount of the pyrimidine derivative described above, and an inert carrier or a diluent; a method for controlling undesirable weeds, which comprises applying the above herbicidal composition to an area where undesirable weeds grow or are likely to grow; and a use of the pyrimidine derivative as a herbicide.

In the formula [1], examples of the $C_1$–$C_6$ alkyl group include methyl, ethyl, n-propyl, isopropyl, n-butyl, sec-butyl, tert-butyl, n-hexyl, etc; examples of the $C_1$–$C_6$ alkoxy group include methoxy, ethoxy, n-propoxy, isopropoxy, n-butoxy, hexyloxy, etc; and examples of the $C_1$–$C_6$ alkoxycarbonyl group include methoxycarbonyl, ethoxycarbonyl, n-butoxycarbonyl, hexyloxycarbonyl, etc.

The halogen atom in the formula [1] includes fluorine, chlorine, bromine and iodine.

When a substituted or unsubstituted $C_2$–$C_6$ oxacycloalkyl $C_1$–$C_6$ alkyl group is selected as A, the examples thereof include oxacyclobutylmethyl, oxacyclobutylethyl, oxacyclobutylpropyl, oxacyclobutylpentyl, oxacyclobutylhexyl, oxacyclopentylmethyl, oxacyclopentylethyl, oxacyclopentylpropyl, oxacyclopentylpentyl, oxacyclopentylhexyl, oxacyclohexylmethyl, oxacyclohexylethyl, oxacyclohexylbutyl, oxacyclohexylpentyl, oxacyclohexylhexyl, oxacycloheptylmethyl, oxacycloheptylethyl, oxacycloheptylbutyl, oxacycloheptylpentyl, oxacycloheptylhexyl, methyloxacyclobutylmethyl, dimethyloxacyclobutylethyl, ethyloxacyclobutylpropyl, hexyloxacyclobutylbutyl, chlorooxacyclobutylpentyl, dichlorooxacyclobutylhexyl, difluorooxacyclopentylmethyl, bromooxacyclopentylethyl, oxacyclopropylmethyl, oxacyclopropylhexyl, etc.

When a substituted or unsubstituted $C_3$–$C_5$ dioxacycloalkyl group is selected as A, the examples thereof include dioxacyclopentyl, dioxacyclohexyl, dioxacycloheptyl, methyldioxacyclopentyl, dimethyldioxacyclohexyl, chlorodioxacycloheptyl group, etc.

When a substituted or unsubstituted $C_3$-$C_5$ dioxacycloalkyl $C_1$-$C_6$ alkyl group is selected as A, the examples thereof include dioxacyclopentylmethyl, dioxacyclopentylethyl, dioxacyclopentylbutyl, dioxacyclopentylpentyl, dioxacyclopentylhexyl, dioxacyclohexylmethyl, dioxacyclohexylethyl, dioxacyclohexylpropyl, dioxacyclohexylpentyl, dioxacyclohexylhexyl, dioxacycloheptylmethyl, dioxacycloheptylethyl, dioxacycloheptylpropyl, dioxacycloheptylpentyl, dioxacycloheptylhexyl, methyldioxacyclopentylmethyl, dimethyldioxacyclohexylmethyl, ethyldioxacycloheptylmethyl, hexyldioxacyclopentylethyl, chlorodioxacyclohexylethyl, dichlorodioxacycloheptylethyl, difluorodioxacyclopentylpropyl, bromodioxacyclohexylpropyl, etc.

When a substituted or unsubstituted $C_3$-$C_6$ oxacycloalkyl group is selected as A, the examples thereof include oxacyclobutyl, oxacyclopentyl, oxacyclohexyl, oxacycloheptyl, methyloxacyclobutyl, dimethyloxacyclopentyl, dichlorooxacyclohexyl, etc.

When a halo $C_1$-$C_6$ alkoxy group is selected as $R^1$ or $R^2$, the examples thereof include fluoromethoxy, difluoromethoxy, trifluoromethoxy, etc.

When a $C_2$-$C_6$ alkenyl group is selected as $Y^4$, the examples thereof include vinyl, allyl, 1-butenyl, 2-butenyl, 3-butenyl, 2-pentenyl, 2-hexenyl, etc.

When a $C_2$-$C_6$ alkynyl group is selected as $Y^4$, the examples thereof include ethynyl, propargyl, 1-butynyl, 2-butynyl, 2-pentynyl, 3-pentynyl, 2-hexynyl, etc.

When a $C_3$-$C_6$ alkenyloxy group is selected as $Y^4$, the examples thereof include allyloxy, 2-butenyloxy, 3-butenyloxy, 2-hexenyloxy, etc.

When a $C_3$-$C_6$ alkynyloxy group is selected as $Y^4$, the examples thereof include propargyloxy, 2-butynyloxy, 3-butynyloxy, 2-hexynyloxy, etc.

When a halo $C_1$-$C_6$ alkyl group is selected as $Y^4$, the examples thereof include fluoromethyl, difluoromethyl, trifluoromethyl, 2-chloroethyl, 3-bromopropyl, etc.

When a halo $C_2$-$C_6$ alkenyl group is selected as $Y^4$, the examples thereof include 1-chlorovinyl, 3-chloroallyl, 5-bromo-2-pentenyl, 6-iodo-2-hexenyl, 5,5,5-trifluoro-2-pentenyl, etc.

When a halo $C_2$-$C_6$ alkynyl group is selected as $Y^4$, the examples thereof include 2-iodoethynyl, 5-bromo-2-pentynyl, 6-iode-2-hexynyl, 5,5,5-trifluoro-2-pentynyl, etc.

When a halo $C_1$-$C_6$ alkoxy group is selected as $Y^4$, the examples thereof include fluoromethoxy, difluoromethoxy, trifluoromethoxy, 1,1,2,2-tetrafluoroethoxy, etc.

When a halo $C_3$-$C_6$ alkenyloxy group is selected as $Y^4$, the examples thereof include 3-chloroallyloxy, 5 bromo-2-pentenyloxy, 6-iodo-2-hexenyloxy, 5,5,5-trifluoro-2-pentenyloxy, etc.

When a halo $C_3$-$C_6$ alkynyloxy group is selected as $Y^4$, the examples thereof include 5-bromo-2-pentynyloxy, 5-chloro-2 pentynyloxy, 3-iodopropargyloxy, etc.

When a $C_1$-$C_6$ alkoxy $C_1$-$C_6$ alkyl group is selected as $Y^4$, the examples thereof include methoxymethyl, ethoxymethyl, 2-methoxyethyl, 4-n-propoxybutyl, 2-n-butoxyethyl, 6-hexyloxyhexyl, etc.

When a $C_3$-$C_6$ alkenyloxy $C_1$-$C_6$ alkyl group is selected as $Y^4$, the examples thereof include allyloxymethyl, 2-allyloxyethyl, 4-allyloxybutyl, 3-(2-butenyloxy)propyl, 6-(hexenyloxy)hexyl, etc.

When a $C_3$-$C_6$ alkynyloxy $C_1$-$C_6$ alkyl group is selected as $Y^4$, the examples thereof include propargyloxymethyl, 2-propargyloxyethyl, 4-propargyloxybutyl, 3-(2-butynyloxy)propyl, 6-2-hexynyloxy)hexyl, etc.

When a $C_3$-$C_6$ alkenyloxycarbonyl group is selected as $Y^4$, the examples thereof include allyloxycarbonyl, 2-butenyloxycarbonyl, 3-butenyloxycarbonyl, 2-hexenyloxycarbonyl, etc.

When a $C_3$-$C_6$ alkynyloxycarbonyl group is selected as $Y^4$, the examples thereof include propargyloxycarbonyl, 2-butynyloxycarbonyl, 3-butynyloxycarbonyl, 2-hexynyloxycarbonyl, etc.

When a substituted phenoxy group is selected as $Y^4$, the examples thereof include 2-methylphenoxy, 3-ethylphenoxy, 4-hexylphenoxy, 2,6-dimethylphenoxy, 3-methoxyphenoxy, 4-isopropoxyphenoxy, 3-hexyloxyphenoxy, 2-trifluoromethylphenoxy, 3-difluoromethylphenoxy, 2-methoxycarbonylphenoxy, 2-ethoxycarbonylphenoxy, 2-n-propoxycarbonylphenoxy, 2-hexyloxycarbonylphenoxy, 2-fluorophenoxy, 2-chlorophenoxy, 3-bromophenoxy, 2,4-dichlorophenoxy, etc.

When a substituted phenyl group is selected as $Y^4$, the examples thereof include 2-methylphenyl, 3-ethylphenyl, 4-hexylphenyl, 2,6-dimethylphenyl, 3-methoxyphenyl, 4-isopropoxyphenyl, 3-hexyloxyphenyl, 2-trifluoromethylphenyl, 3-difluoromethylphenyl, 2-methoxycarbonylphenyl, 2-ethoxycarbonylphenyl, 2-n-propoxycarbonylphenyl, 2-hexyloxycarbonylphenyl, 2-fluorophenyl, 2-chlorophenyl, 3-bromophenyl, 2,4-dichlorophenyl, etc.

When a substituted phenylthio group is selected as $Y^4$, the examples thereof include 2-methylphenylthio, 3-ethylphenylthio, 4-hexylphenylthio, 2,6-dimethylphenylthio, 3-methoxyphenylthio, 4-isopropoxy-phenylthio, 3-hexyloxyphenylthio, 2-trifluoromethylphenylthio, 3-difluoromethylphenylthio, 2-methoxycarbonylphenylthio, 2-ethoxycarbonylphenylthio, 2-n-propoxycarbonylphenylthio, 2-hexyloxycarbonylphenylthio, 2-fluorophenylthio, 2-chlorophenylthio, 3-bromophenylthio, 2,4-dichlorophenylthio, etc.

When a substituted benzyloxy group is selected as $Y^4$, the examples thereof include 2-methylbenzyloxy, 3-ethylbenzyloxy, 4-hexylbenzyloxy, 2,6-dimethylbenzyloxy, 3-methoxybenzyloxy, 4-isopropoxybenzyloxy, 3-hexyloxybenzyloxy, 2-trifluoromethylbenzyloxy, 3-difluoromethylbenzyloxy, 2-methoxycarbonylbenzyloxy, 2-ethoxycarbonylbenzyloxy, 2-n-propoxycarbonylbenzyloxy, 2-hexyloxycarbonylbenzyloxy 2-fluorobenzyloxy, 2-chlorobenzyloxy, 3-bromobenzyloxy, 2,4-dichlorobenzyloxy, etc.

When a substituted benzylthio group is selected as $Y^4$, the examples thereof include 2-methylbenzylthio, 3-ethylbenzylthio, 4-hexylbenzylthio, 2,6-dimethylbenzylthio, 3-methoxybenzylthio, 4-isopropoxybenzylthio, 3-hexyloxybenzylthio, 2-trifluoromethylbenzylthio, 3-difluoromethylbenzylthio, 2-methoxycarbonylbenzylthio, 2-ethoxycarbonylbenzylthio, 2-n-propoxycarbonylbenzylthio, 2-hexyloxycarbonylbenzylthio, 2-fluorobenzylthio, 2-chlorobenzylthio, 3-bromobenzylthio, 2,4-dichlorobenzylthio, etc.

When a $C_3$-$C_6$ alkenyl group is selected as $R^5$, $R^6$ or $R^7$, the examples thereof include allyl, 1-butenyl, 2-butenyl, 3-butenyl, 2-pentenyl, 2-hexenyl, etc.

When a $C_3$-$C_6$ alkynyl group is selected as $R^5$, $R^6$ or $R^7$, the examples thereof include propargyl, 1-butynyl, 2-butynyl, 2-pentynyl, 3-pentynyl, 2-hexynyl, etc.

In the compound of the formula (I), the substituents $R^1$ and $R^2$, which may be the same or different, are preferably $C_1$-$C_6$ alkoxy, and more preferably, both of them are methoxy.

A is preferably a $C_3$-$C_5$ dioxacycloalkyl $C_1$-$C_6$ alkyl group. More preferably, A is 1,3-dioxolane-2-yl $C_1$-$C_6$ alkyl group or 1,3-dioxan-2-yl $C_1$-$C_6$ alkyl group. Most preferably, A is 1,3-dioxolane-2-yl ethyl group or 1,3-dioxan-2-yl ethyl group. X is preferably oxygen.

Z is preferably nitrogen or $CY^5$ wherein $Y^5$ is hydrogen or halogen, a halo $C_1$-$C_6$ alkyl group, a $C_1$-$C_6$ alkyl group, a $C_1$-$C_6$ alkoxy group or a substituted or unsubstituted phenyl group. More preferably, Z is nitrogen or $CY^5$ in which $Y^5$ is hydrogen or halogen.

$Y^1$ and $Y^2$, which may be the same or different, are preferably a hydrogen atom or a fluorine atom.

$Y^3$ is preferably hydrogen, fluorine or a $C_1$-$C_6$ alkoxy group. Specific examples of the pyrimidine derivative of the present invention include 2-(1,3-dioxan-2-yl)ethyl 2-(4,6-dimethoxypyrimidin-2-yl)oxybenzoate,

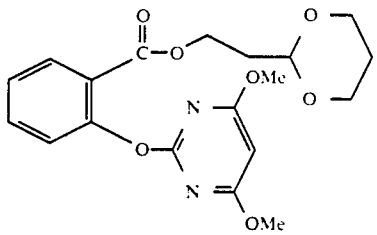

2-(1,3-dioxan-2-yl)ethyl 2-chloro-6-(4,6-dimethoxypyrimidin-2-yl)oxybenzoate.

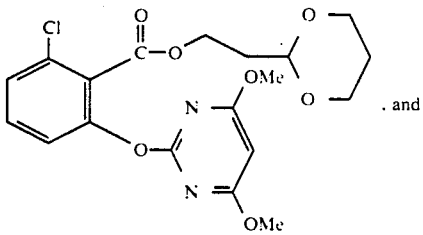

2-(1,3-dioxan-2-yl)ethyl 3-(4,6-dimethoxypyrimidin-2-yl)oxypicolinate,

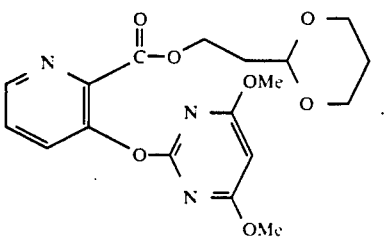

A method for producing the present compound is as follows.

The present compound (1) can be produced by reacting a compound represented by the formula (2),

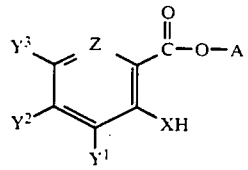

wherein A, X, $Y^1$, $Y^2$, $Y^3$ and Z are as defined above, with a compound represented by the formula (3),

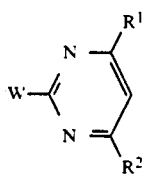

wherein $R^1$, $R^2$ and W are as defined above.

This reaction is usually carried out with or without a solvent in the presence of a base. The reaction temperature usually ranges from room temperature to the boiling point of the solvent, and the reaction time usually ranges from 10 minutes to 24 hours. Referring to the amounts of the reagents used for this reaction, the amount of the compound (3) is usually 1.0 to 1.5 equivalents based on 1 equivalent of the compound (2), and that of the base is usually 1.0 to 5.0 equivalents based on the same. The solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), alcohols (e.g. methanol, ethanol, isopropanol, tert-butanol, octanol, cyclohexanol, methyl cellosolve, diethylene glycol, glycerin), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), liquid ammonia, water and the mixtures thereof.

Specific examples of the base are organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction solution may be after-treated as usual. That is, water is added to the solution which is then extracted with an organic solvent and concentrated, and if necessary, the product obtained is subjected to chromatography, distillation, recrystallization, etc. Thus, the desired present compound can be obtained.

The compound represented by the formula (3) can be produced according to Japanese Patent Application Kokai No. 63-23870, J. Org. Chem., 26, 792 (1961), etc.

The present compound can also be produced by reacting a compound represented by the formula (4),

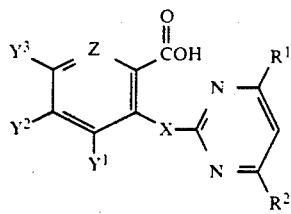 (4)

wherein $R^1$, $R^2$, X, $Y^1$, $Y^2$, $Y^3$ and Z are as defined above, with an acid-halogenating agent or an active esterifying agent (hereinafter reaction (i)), and reacting the resulting reaction product with an alcohol derivative represented by the formula (5), <p align="center">HO—A        (5)</p> wherein A is as defined above (hereinafter reaction (ii)).

In the above reaction (i), specific examples of the acid halogenating agent are thionyl chloride, thionyl bromide, phosphorus trichloride, phosphorus tribromide, phosphorus pentachloride, phosphorus oxychloride, phosgene, oxalic acid dichloride, etc. Specific examples of the active esterifying agent are N,N'-disubstituted carbodiimides such as N,N'-dicyclohexylcarbodiimide, N,N'-diisopropylcarbodiimide, 1-ethyl-3-(3-dimethylaminopropyl)carbodiimide hydrochloride, etc.; arylsulfonyl chlorides such as 2,4,6-trimethylbenzenesulfonyl chloride, 2,4,6-triisopropylbenzenesulfonyl chloride, etc.; N,N'-carbonyldiimidazole; diphenylphosphorylazide; N-ethoxycarbonyl-2-ethoxy-1,2-dihydroquinoline; N-ethyl-2'-hydroxybenzisoxazolium trifluoroborate; N-ethyl-5-phenylisoxazolium-3'-sulfonate; etc.

By this reaction, a compound represented by the formula (6),

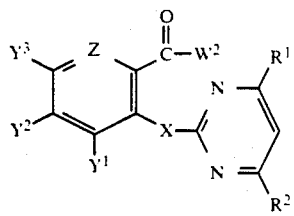 (6)

wherein $R^1$, $R^2$, X, $Y^1$, $Y^2$, $Y^3$ and Z are as defined above, is produced in the reaction system.

In the above formula (6), a substituent $W^2$ represents a halogen atom when the acid-halogenating agent was used; $W^2$ represents an N,N'-disubstituted-2-isoureido group when N,N'-disubstituted carbodiimide was used as the active esterifying agent; $W^2$ represents an arylsulfonyloxy group when arylsulfonyl chloride was used as said agent; $W^2$ represents an imidazolyl group when N,N'-carbonyldiimidazole was used as said agent; $W^2$ represents an azide group when diphenylphosphorylazide was used as said agent; $W^2$ represents an ethoxycarbonyloxy group when N-ethoxycarbonyl-2-ethoxy-1,2-dihydroquinoline was used as said agent; $W^2$ represents a 3-(N-ethylaminocarbonyl)-2-hydroxyphenoxy group when N-ethyl-2'-hydroxybenzisoxazolium trifluoroborate was used as said agent; and $W^2$ represents a group

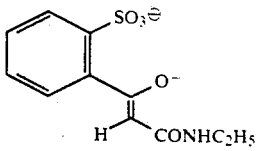

when N-ethyl-5-phenylisoxazoli-m-3'-sulfonate was used as said agent.

In the reaction system, $W^2$ can also take a form of acid anhydride containing the moiety represented by the formula,

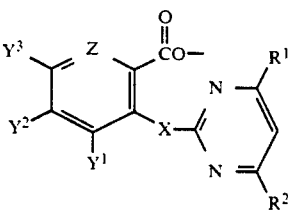

wherein $R^1$, $R^2$, X, $Y^1$, $Y^2$, $Y^3$ and Z are as defined above.

The amount of the foregoing acid-halogenating agent or active esterifying agent used is usually 1 to 10 equivalents based on 1 equivalent of the compound represented by the formula (4).

The amount of the alcohol derivative of the formula (5) used is usually 1 to 5 equivalents based on 1 equivalent of the compound represented by the formula (4).

The reactions (i) and (ii) can also be carried out, if necessary, in the presence of a base. Such a base includes organic bases (e.g. 1-methylimidazole, 3-nitro-1H-1,2,4-triazole, 1H-tetrazole, 1H-1,2,4-triazole, imidazole, pyridine, triethylamine) and inorganic bases (e.g. potassium carbonate). The amount of the base used is usually 1 to 20 equivalents based on 1 equivalent of the compound represented by the formula (4).

The reactions (i) and (ii) are usually carried out in the presence of an inert solvent. Such a solvent includes aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. N,N-dimethylformamide), sulfur compounds (e.g. dimethyl sulfoxide, sulfolane) and the mixtures thereof.

Generally, the reaction temperature usually ranges from 0° C. to the boiling point of the solvent in any of the reactions (i) and (ii). The reaction time usually ranges from 1 to 24 hours for each reaction, and from about 1 to about 48 hours through the reactions (i) and (ii).

After completion of the reaction, the reaction solution may be after-treated as usual. That is, water is added to the solution which is then extracted with an organic solvent and concentrated, and if necessary, the product obtained is subjected to the chromatography, distillation, recrystallization, etc. Thus, the desired present compound can be obtained.

The present compound can also be prepared by reacting a compound represented by the formula (4), with a halide represented by the formula (7)

$$W^3-A \quad (7)$$

wherein A and $W^3$ are as defined above.

This reaction is usually carried out with or without a solvent in the presence of a base. The reaction temperature usually ranges from room temperature to the boiling point of the solvent, and the reaction time usually ranges from 30 minutes to 24 hours. Referring to the amounts of the reagents used for this reaction, the amount of the halide (7) is usually 1.0 to 5.0 equivalents based on 1 equivalent of the compound (4), and that of the base is usually 1.0 to 5.0 equivalents based on the same. Examples of the solvent include aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether) and ketones (e.g. acetone, methyl ethyl ketone, methyl isobutyl ketone, isophorone, cyclohexanone), esters (e.g. ethyl formate, ethyl acetate, butyl acetate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethyl sulfoxide, sulfolane), and mixtures thereof.

The base includes organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction solution is after-treated as usual. That is, water is added to the solution which is then extracted with an organic solvent and concentrated, and if necessary, the product obtained is subjected to chromatography, distillation, recrystallization, etc. Thus, the desired present compound can be obtained.

The compound represented by the formula (4) can be produced according to EP 0 223 406 A1, etc.

In producing the present compounds, when the compound (a starting material for compound (1)), represented by the formula (2) is other than the compounds in which $Y^4$ is a group,

in which $R^6$ is as defined above, or a group,

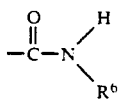

in which $R^6$ is as defined above, said compound can be produced as follows: The method comprises reacting an aromatic carboxylic acid halide represented by the following formula (8),

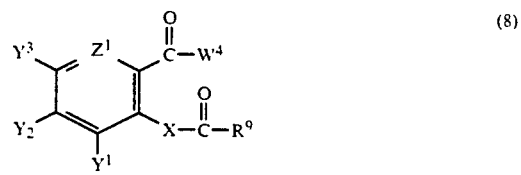

wherein X, $Y^1$, $Y^2$ and $Y^3$ are as defined above, $W^4$ represents a halogen atom, $R^9$ represents a $C_1$-$C_6$ alkyl group, and $Z^1$ represents $CY_4'$ wherein $Y^{4'}$ is hydrogen, nitro, halogen, $C_1$-$C_6$ alkyl, $C_2$-$C_6$ alkenyl, $C_2$-$C_6$ alkynyl, $C_1$-$C_6$ alkoxy, $C_3$-$C_6$ alkenyloxy, $C_3$-$C_6$ alkynyloxy, halo $C_1$-$C_6$ alkyl, halo $C_2$-$C_6$ alkenyl, halo $C_2$-$C_6$ alkynyl, halo $C_1$-$C_6$ alkoxy, halo $C_3$-$C_6$ alkenyloxy, halo $C_3$-$C_6$ alkynyloxy, $C_1$-$C_6$ alkoxy $C_1$-$C_6$ alkyl, $C_3$-$C_6$ alkenyloxy $C_1$-$C_6$ alkyl, $C_3$-$C_6$ alkynyloxy $C_1$-$C_6$ alkyl, cyano, formyl, carboxyl, $C_1$-$C_6$ alkoxycarbonyl, $C_3$-$C_6$ alkenyloxycarbonyl, $C_3$-$C_6$ alkynyloxycarbonyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenoxy, phenoxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, phenylthio, phenylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzyloxy, benzyloxy substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, benzylthio, benzylthio substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen,

wherein each of $R^{5'}$ and $R^{6'}$, which may be the same or different, is $C_1$-$C_6$ alkyl, $C_3$-$C_6$ alkenyl or $C_3$-$C_6$ alkynyl,

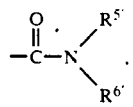

wherein $R^{5'}$ and $R^{6'}$ are as defined above,

wherein $R^7$ and m are as defined above,

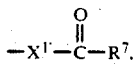

wherein $R^7$ and $X^1$ are as defined above, or

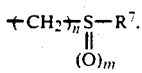

wherein $R^7$, m and n are as defined above, or a group represented by the formula,

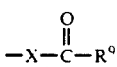

in which $R^9$ and X are as defined above, with the alcohol derivative represented by the formula (5) in the presence of a dehydrohalogenating agent and hydrolyzing the resulting compound with a base (e.g. sodium hydroxide, potassium hydroxide) or an acid (e.g. hydrochloric acid, sulfuric acid) to remove the group,

Or alternatively, the method comprises reacting a compound represented by the formula,

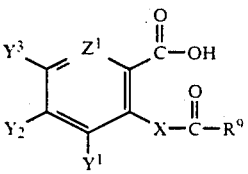

wherein X, $Y^1$, $Y^2$, $Y^3$, $Z^1$ and $R^9$ are as defined above, with the compound (7),

     (7)

in the presence of a dehydrohalogenating agent and hydrolyzing the resulting compound with a base (e.g. sodium hydroxide, potassium hydroxide) or an acid (e.g. hydrochloric acid, sulfuric acid) to remove the group,

Specific examples of the dehydrohalogenating agent are pyridine, triethylamine, N,N-diethylaniline, etc.

After completion of the reaction, the reaction solution may be after-treated as usual. That is, water is added to the solution which is then extracted with an organic solvent and concentrated, and if necessary, the product obtained is subjected to the chromatography, distillation, recrystallization, etc. Thus, the compound (2) can be obtained.

The compound represented by the formula (2) can be produced by reacting an aromatic carboxylic acid derivative represented by the formula (g),

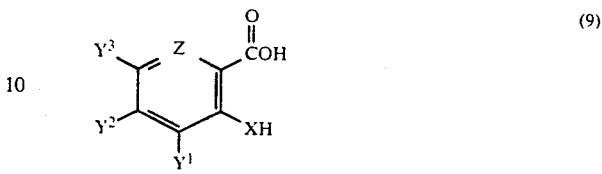

wherein X, $Y^1$, $Y^2$, $Y^3$ and Z are as defined above, with an acid halogenating agent or an active esterifying agent (hereinafter reaction (iii)), and reacting the resulting reaction product with the alcohol derivative represented by the formula (5) (hereinafter reaction (iv)).

The above reactions (iii) and (iv) can be carried out according to the foregoing reactions (i) and (ii), respectively. The aromatic carboxylic acid halide derivative (8) can be produced according to Beilstein H10/p.86, EI10/p.43, EII10/p.55, EIII10/p.151, EIV10/p.169, etc.

The aromatic carboxylic acid derivative (9) can be produced according to J. Org. Chem., 27, 3551 (1962), Chem. Pharm. Bull., 31, 407 (1983), Yakugaku Zasshi, 99, 657 (1979), Chem. Pharm. Bull., 27, 1468 (1979), J. Med. Chem., 21, 1093 (1978), Yakugaku Zasshi, 92, 1386 (1972), Eur. J. Med. Chem-Chim. Ther., 21, 379 (1986), J. Chem. Soc., Perkin Trans. 1, 2069 (1979), J. Chem. Soc., Perkin Trans. 1, 2079 (1979), J. Chem. Soc., Chem. Commun., 1127 (1968), J. Med. Chem., 31, 1039 (1988), Indian J. Chem., 25B, 796 (1986), J. Am. Chem. Soc., 107, 4593 (1985), J. Org. Chem., 50, 718 (1985), J. Agric. Food Chem., 32, 747 (1984), J. Pharm. Pharmacol., 35, 718 (1983), J. Org. Chem., 48, 1935 (1983), J. Chem. Soc., Chem. Commun., 1974, 362, etc.

Compound (1) and Compound (2) include their stereo isomers having a herbicidal activity.

The present compounds (1) have an excellent herbicidal activity and some of them have an excellent selectivity to the undesired weeds as compared with the desired crops.

That is, the present compound, when used for foliar treatment and soil treatment in upland fields, exhibits a herbicidal activity against a wide variety of undesired weeds. Also, the present compound (1), when used for flooding treatment in paddy fields, exhibits a herbicidal activity against a wide variety of undesired weeds.

The present compound (1) can control a wide range of weeds generated in crop lands or non-crop lands, can be applied in low dosage rates, has a broad herbicidal spectrum and also can safely be used for no-till cultivation in soybean fields, peanut fields, corn fields, etc.

As weeds which can be controlled by the present compound, there are mentioned for example broad-leaved weeds such as wild buckwheat (*Polygonum convolvulus*), pale smartweed (*Polygonum lapathifolium*), common purslane (*Portulaca oleracea*), chickweed (*Stellaria media*), common lambsquarters (*Chenopodium album*), redroot pigweed (*Amaranthus retroflexus*), radish (*Raphanus sativus*), wild mustard (*Sinapis arvensis*), shepherds purse (*Capsella bursa-pastoris*), hemp sesbania (*sesbania exaltata*), sicklepod (*Cassia obtusifolia*), velvetleaf (*Abutilon theophrasti*), prickly sida (*Sida spinosa*), field pansy (*Viola arvensis*), cleavers (*Galium aparine*), ivyleaf morningglory (*Ipomoea hederacea*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum niqrum*), birdseye speedwell (*Veronica persica*), cocklebur (*Xanthium strumarium*), sunflower (*Helianthus annuus*), scentless chamomile (*Matricaria perforata*), corn marigold (*Chrysanthemum seqetum*), etc.; Gramineae weeds such as Japanese millet (*Echinochloa frumentacea*), barnyardgrass (*Echinochloa crus-qalli*), green foxtail (*Setaria viridis*), giant foxtail (*Setaria faberi*), large crabgrass (*Digitaria sanquinalis*), annual bluegrass (*Poa annua*), blackgrass (*Alopecurus myosuroides*), oat (*Avena sativa*), wild oat (*Avena fatua*), johnsongrass (*Sorghum halepense*), quackgrass (*Agropyron repens*), downy brome (*Bromus tectorum*), bermudagrass (*Cynodon dactylon*), etc.; Commelinaceae weeds such as dayflower (*Commelina communis*), etc.; and Cyperaceae weeds such as rice flatsedge (*Cyperus iria*), purple nutsedge (*Cyperus rotundus*), etc. In addition, the present compounds give such no phytotoxicity as becoming a problem to main crops such as corn, wheat, barley, rice, soybean, cotton, beet, etc.

In flooding treatment in paddy fields, the present compounds exhibit a herbicidal activity against gramineous weeds such as barnyardgrass (*Echinochloa oryzicola*), etc.; broad-leaved weeds such as false pimpernel (*Lindernia procumbens*), indian toothcup (*Rotala indica*), waterwort (*Elatine triandra*), *Ammannia multiflora*, etc.; Cyperaceae weeds such as smallflower umbrellaplant (*Cyperus difformis*), bulrush (*Scirpus juncoides*), slender spikerush (*Eleocharis acicularis*), water nutgrass (*Cyperus serotinus*), etc.; monochoria (*Monochoria vaginalis*), arrowhead (*Sagittaria pyqmaea*), etc.

When the present compound (1) is used as an active ingredient for herbicides, it is usually formulated before use into emulsifiable concentrates, wettable powders, suspension formulations, granules, water-dispersible granules, etc. by mixing the present compound (1) with solid carriers, liquid carriers, surface active agents or other auxiliaries for formulation.

The content of the compound (1) as an active ingredient in these preparations is normally within a range of about 0.001 to 90% by weight, preferably of about 0.003 to 80% by weight.

Examples of the solid carriers are fine powders or granules of kaolin clay, attapulgite clay, bentonite, terra alba, pyrophyllite, talc, diatomaceous earth, calcite, walnut shell powders, urea, ammonium sulfate and synthetic hydrated silicon dioxide, etc.

Examples of the liquid carriers are aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (soybean oil, cotton seed oil), dimethyl sulfoxide, N,N-dimethylformamide, acetonitrile, water, etc.

Examples of the surface active agents used for emulsification, dispersion or spreading, etc. are anionic surface active agents such as salts of alkyl sulfates, alkylsulfonates, alkylarylsulfonates, dialkyl sulfosuccinates, salts of polyoxyethylene alkylaryl ether phosphoric acid esters, etc., and nonionic surface active agents such as polyoxyethylene alkyl ethers, polyoxyethylene alkylaryl ethers, polyoxyethylene polyoxypropylene block copolymers, sorbitan fatty acid esters, polyoxyethylene sorbitan fatty acid esters, etc.

Examples of the other auxiliaries for formulation are lignosulfonates, alginates, polyvinyl alcohol, gum arabic, CMC (carboxymethyl cellulose), PAP (isopropyl acid phosphate), etc.

The present compound (1) is usually formulated into an appropriate formulation and used in soil treatment, foliar treatment or flooding treatment before or after emergence of weeds. The soil treatment includes soil surface treatment and soil incorporation treatment. The foliar treatment includes, in addition to the treatments of plants mentioned above, direct treatment in which the formulation is applied only to weeds so as to prevent the formulation from adhering to crops.

The herbicidal activity of the present compound (1) can be expected to be increased by using the compound in mixture with other herbicides. Further, the present compound (1) can also be used in mixture with insecticides, acaricides, nematocides, fungicides, plant growth regulators, fertilizers, soil improvers, etc.

The present compound (1) can be used as an active ingredient for herbicides used in paddy fields, ridges of paddy fields, plowed fields, fields other than plowed fields, orchards, pastures, turfs, forests and fields other than agricultural fields, etc.

When the present compound (1) is used as an active ingredient for herbicides, the dosage rate varies depending upon the weather conditions, preparation forms, when, how and where the treatment is carried out, weeds species to be controlled, crops species to be protected, etc. Usually, however, the dosage rate is from 0.003 grams to 100 grams of the active ingredient per are, preferably from 0.01 grams to 50 grams of the active ingredient per are.

The herbicidal composition of the invention formulated in the form of an emulsifiable concentrate, a wettable powder or a suspension formulations may ordinarily be employed after diluting it with water at a volume of about 1 to 10 liters per are. If necessary, auxiliaries such as a spreading agent are added to the water. The granules are usually applied as they are without being diluted.

Examples of the spreading agent are, in addition to the foregoing surface active agents, substances such as polyoxyethylene resin acids (esters), lignosulfonates, abietates, dinaphthylmethanedisulfonates, paraffin, etc.

The present invention will be illustrated in more detail with reference to the following production examples, formulation examples and test examples, which are not however to be interpreted as limiting the invention thereto.

First, production examples for the present compound (1) are shown.

PRODUCTION EXAMPLE 1

0.84 Gram of 2-(1,3-dioxan-2-yl)ethyl 5 salicylate and 0.73 g of 4,6-dimethoxy-2-methylsulfonylpyrimidine was dissolved in 10 ml of N,N-dimethylformamide, and 0.51 g of anhydrous potassium carbonate was added thereto. The resulting solution was stirred at 100° to 110° C. for 1 hour. The reaction solution was allowed to cool, poured into diluted hydrochloric acid, and extracted with ethyl acetate. The organic layer separated from the aqueous layer was washed with saturated sodium chloride solution and dried over anhydrous magnesium sulfate. The solvent was removed under reduced pressure, and the residue obtained was subjected to silica gel column chromatography (mfd by Merck & Co., Inc., solvent: chloroform) to obtain 0.50 g of 2-(1,3- dioxan-2-yl)ethyl 2-(4,6-dimethoxypyrimidin-2-yl)oxybenzoate [present compound (V-1)].

¹H-NMR (CDCl₃) δ: 1.28–2.23 (m, 4H); 3.61–4.45 (m, 7H); 3.75 (s, 6H); 5.71 (s, 1H); 7.07–8.04 (m, 4H)

PRODUCTION EXAMPLE 2

10 Milliliters of N,N-dimethylformamide in which 0.22 g of 60% sodium hydride in oil has been suspended was mixed with 5 ml of N,N-dimethylformamide solution of 1.38 g of 2-(4,6-dimethoxypyrimidin-2-yl)oxy benzoic acid. After stirring the mixture at room temperature for 30 minutes, 10 ml of N,N-dimethylformamide solution of 1.81 g of 2-(2-bromoethyl)-1,3-dioxolane was added thereto. The resulting solution was stirred at 100° to 110° C. for 2 hours. The reaction solution was allowed to cool, poured into diluted hydrochloric acid, and extracted with ethyl acetate. The organic layer separated from the aqueous layer was washed with saturated sodium chloride solution and dried over anhydrous magnesium sulfate. The solvent was removed under reduced pressure, and the residue obtained was subjected to silica gel column chrmatography (mfd. by Merck & Co., Inc., solvent: chloroform) to obtain 1.20 g of 2-(1,3-dioxolan-2-yl)ethyl 2-(4,6-dimethoxypyrimidin-2-yl)oxybenzoate [present compound (V-2)].

¹H-NMR (CDCl₃) δ: 1.71–2.31 (m, 2H); 3.68–3.93 (m, 4H); 3.73 (s, 6H); 4.21 (t, 2H, J=6.4Hz); 4.79 (t, 1H, J=5.0Hz); 5.67 (s, 1H); 7.08–7.98 (m, 4H)

PRODUCTION EXAMPLE 3

0.55 Gram of 2-(4,6-dimethoxypyrimidin-2-yl)oxybenzoic acid, 0.21 g of tetrahydrofurfuryl alcohol and 0.85 g of 2,4,6-triisopropylbenzenesulfonyl chloride were dissolved in 5 ml of tetrahydrofuran. Subsequently, 0.45 g of 1-methylimidazole was added to the mixture. After stirring the resulting solution at room temperature for 1 hour in order to carry out the reaction, the reaction solution was poured into diluted hydrochloric acid, and extracted with ethyl acetate. The organic layer separated from the aqueous layer was washed with saturated sodium chloride solution and dried over anhydrous magnesium sulfate. The solvent was removed under reduced pressure, and the residue obtained was subjected to silica gel column chromatography (mfd. by Merck & Co., Inc., solvent: chloroform) to obtain 0.30 g of tetrahydrofurfuryl 2-(4,6-dimethoxypyrimidin-2-yl)oxybenzoate [present compound (III-g)].

¹H-NMR (CDCl₃) δ: 1.45–2.15 (m, 4H); 3.65–4.20 (m, 5H); 3.76 (s, 6H); 5.73 (s, 1H); 7.12–8.10 (m, 4H);

PRODUCTION EXAMPLE 4

According to the procedure shown in Production Example 2, 2-(1,3-dioxan-2-yl)ethyl 6-fluoro-2-(4,6-dimethoxypyrimidin-2-yl)oxybenzoate (present compound (V-24)) can be obtained by reacting 2.94 g of 2-fluoro-6-(4,6-dimethoxypyrimidin-2-yl)oxybenzoic acid, 0.44 g of sodium hydride in oil and 5.85 g of 2-(bromoethyl)-1,3-dioxane. 1,3-dioxane.

PRODUCTION EXAMPLE 5

According to the procedure shown in Production Example 2, 2-(1,3-dioxan-2-yl)ethyl 2-(4,6-dimethoxypyrimidin-2-yl)oxy-6-phenylbenzoate (present compound (V-49)) can be obtained by reacting 3.52 g of 2-(4,6-dimethoxypyrimidin-2-yl)oxy-6-phenylbenzoic acid, 0.44 g of sodium hydride in oil and 5.85 g of 2-(bromoethyl)-1,3-dioxane.

PRODUCTION EXAMPLE 6

According to the procedure shown in Production Example 2, 2-(1,3-dioxan-2-yl)ethyl 6-methoxy-2-(4,6-dimethoxypyrimidin-2-yl)oxybenzoate (present compound (V-31)) can be obtained by reacting 3.06 g of 2-methoxy-6-(4,6-dimethoxypyrimidin-2-yl)oxybenzoic acid, 0.44 g of sodium hydride in oil and 5.85 g of 2-(bromoethyl)-1,3-dioxane.

PRODUCTION EXAMPLE 7

According to the procedure shown in Production Example 2, 2-(1,3-dioxan-2-yl)ethyl 2-(4,6-dimethoxypyrimidin-2-yl)oxy-6-methylbenzoate (present compound (V-34) can be obtained by reacting 2.94 g of 2-(4,6-dimethoxypyrimidin-2-yl)oxy-6-methylbenzoic acid, 0.44 g of sodium hydride in oil and 5.85 g of 2-(bromoethyl)-1,3-dioxane.

PRODUCTION EXAMPLE 8

According to the procedure shown in Production Example 2, 2-(1,3-dioxan-2-yl)ethyl 2-(4,6-dimethoxypyrimidin-2-yl)oxy-6-trifluoromethylbenzoate (present compound (V-33)) can be obtained by reacting 2.94 g of 2-(4,6-dimethoxypyrimidin-2-yl)oxy-6-trifluoromethylbenzoic acid, 0.44 g of sodium hydride in oil and 5.85 g of 2-(bromoethyl)-1,3-dioxane.

Table 1 illustrates specific examples of the compound (1), which can be produced by using the corresponding starting compounds. Compounds (V-2), (V-10), (V-14) to (V-23) were prepared according to the procedure of Production Example 2. Compounds (II-3), (V-4), (III-5), (III-7), (V-8), (IV-11), and (III-9) were prepared according to the procedure of Production Example 3.

TABLE 1

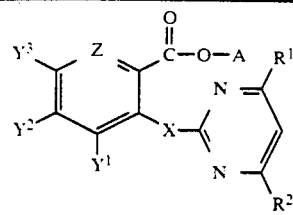

| Compound No. | A | $Y^1$ | $Y^2$ | $Y^3$ | X | Z | $R^1$ | $R^2$ | Physical properties (m.p., refractive index) |
|---|---|---|---|---|---|---|---|---|---|
| (II-1) | oxetanyl | H | H | H | O | CF | $OCH_3$ | $OCH_3$ | |
| (II-2) | oxetanyl | H | H | H | O | CCl | $OCH_3$ | $OCH_3$ | |
| (II-3) | tetrahydrofuranyl | H | H | H | O | CH | $OCH_3$ | $OCH_3$ | $n_D^{24}$ 1.5355 |
| (II-4) | tetrahydrofuranyl | H | H | H | S | CCl | $OCH_3$ | $OCH_3$ | |
| (II-5) | tetrahydrofuranyl | H | H | H | O | CBr | $OCH_3$ | $OCH_3$ | |
| (II-6) | tetrahydrofuranyl | H | H | H | S | CBr | $OCH_3$ | $OCH_3$ | |
| (II-7) | tetrahydropyranyl | H | H | H | O | $COCH_3$ | $OCH_3$ | $OCH_3$ | |
| (II-8) | tetrahydropyranyl | H | H | H | O | CCl | $OCH_3$ | $OCH_3$ | |
| (II-9) | tetrahydropyranyl | H | H | H | O | CCl | $CH_3$ | $OCH_3$ | |
| (II-10) | tetrahydropyranyl | H | H | H | O | CF | Cl | $OCH_3$ | |
| (II-11) | tetrahydropyranyl | H | H | H | O | N | Cl | Cl | |

TABLE 1-continued

Structure:
Y³–Z=C(−O−A)... aromatic ring with Y¹, Y², Y³, linked via X to pyrimidine bearing R¹ and R² (with C=O above).

| Compound No. | A | Y¹ | Y² | Y³ | X | Z | R¹ | R² | Physical properties (m.p., refractive index) |
|---|---|---|---|---|---|---|---|---|---|
| (I-12) | oxepane (7-membered ring with O) | H | H | H | O | CCF₃ | OCH₃ | OCH₃ | |
| (II-13) | oxepane | H | H | H | O | CCH₃ | OCH₃ | OCH₃ | |
| (II-14) | oxepane | H | H | H | O | CC₆H₅ | OCH₃ | OCH₃ | |
| (II-15) | tetrahydropyranyl | H | H | H | O | CNO₂ | OCH₃ | OCH₃ | |
| (II-16) | tetrahydropyranyl | H | H | F | O | CCl | OCH₃ | OCH₃ | |
| (III-1) | CH₂–oxiranyl | H | H | H | O | N | OCH₃ | OCH₃ | |
| (III-2) | CH₂–oxiranyl | H | H | H | O | CF | OCH₃ | OCH₃ | |
| (III-3) | CH₂–oxiranyl | H | H | H | O | CCl | OCH₃ | OCH₃ | |
| (III-4) | CH₂–oxiranyl | H | H | H | S | CCl | OCH₃ | OCH₃ | |
| (III-5) | CH₂–oxiranyl | H | H | H | O | CH | OCH₃ | OCH₃ | $n_D^{22.5}$ 1.5391 |
| (III-6) | CH₂–oxetanyl | H | H | H | S | CBr | OCH₃ | OCH₃ | |

TABLE 1-continued
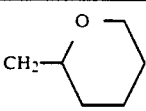
| Compound No. | A | Y¹ | Y² | Y³ | X | Z | R¹ | R² | Physical properties (m.p., refractive index) |
|---|---|---|---|---|---|---|---|---|---|
| (III-7) | 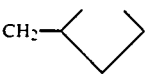 | H | H | H | O | CH | OCH₃ | OCH₃ | $n_D^{22.5}$ 1.5335 |
| (III-8) | 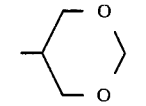 | H | H | H | O | CCl | OCH₃ | OCH₃ | |
| (IV-1) | 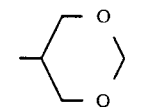 | H | H | H | O | N | OCH₃ | OCH₃ | |
| (IV-2) | 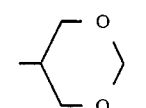 | Cl | H | H | O | CF | OCH₃ | OCH₃ | |
| (IV-3) | 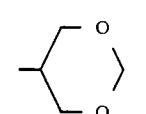 | H | CH₃ | H | O | CCl | OCH₃ | OCH₃ | |
| (IV-4) | 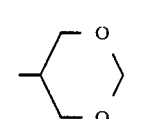 | H | H | OCH₃ | S | CCl | OCH₃ | OCH₃ | |
| (IV-5) | 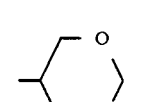 | H | H | F | O | CBr | OCH₃ | OCH₃ | |
| (IV-6) | 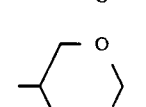 | C₂H₅ | H | H | S | CBr | OCH₃ | OCH₃ | |
| (IV-7) | 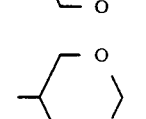 | H | Cl | H | O | COCH₃ | OCH₃ | OCH₃ | |
| (IV-8) | 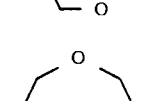 | H | H | F | O | CCF₃ | OCH₃ | OCH₃ | |
| (IV-9) | | H | H | H | O | CCl | OCH₃ | OCH₃ | |

TABLE 1-continued

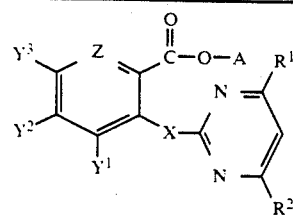

| Compound No. | A | $Y^1$ | $Y^2$ | $Y^3$ | X | Z | $R^1$ | $R^2$ | Physical properties (m.p., refractive index) |
|---|---|---|---|---|---|---|---|---|---|
| (IV-10) | ![structure with O, CH3, CH3, O] | H | H | H | O | CF | $OCH_3$ | $OCH_3$ | |
| (IV-11) | ![structure with O, O] | H | H | H | O | CH | $OCH_3$ | $OCH_3$ | m.p. 118–119° C. |
| (IV-12) | ![structure with O, CH3, CH3, O] | H | H | H | S | CCl | $OCH_3$ | $OCH_3$ | |
| (IV-13) | ![structure with O, CH3, CH3, O] | H | H | H | O | CBr | $OCH_3$ | $OCH_3$ | |
| (IV-14) | ![structure with O, CH3, C2H5, O] | H | H | H | S | CBr | $OCH_3$ | $OCH_3$ | |
| (IV-15) | ![structure with O, C2H5, C2H5, O] | H | H | H | O | $COCH_3$ | $OCH_3$ | $OCH_3$ | |
| (IV-16) | ![structure with O, C2H5, C3H7(n), O] | H | H | H | O | CCl | $OCH_3$ | $OCH_3$ | |
| (V-1) | $CH_2CH_2-$![dioxane ring] | H | H | H | O | CH | $OCH_3$ | $OCH_3$ | $n_D^{24}$ 1.5341 |
| (V-2) | $CH_2CH_2-$![dioxolane ring] | H | H | H | O | CH | $OCH_3$ | $OCH_3$ | $n_D^{22}$ 1.5325 |
| (V-3) | $CH_2-$![dioxolane ring] | H | H | H | O | CCl | $OCH_3$ | $OCH_3$ | |

TABLE 1-continued

| Compound No. | A | $Y^1$ | $Y^2$ | $Y^3$ | X | Z | $R^1$ | $R^2$ | Physical properties (m.p., refractive index) |
|---|---|---|---|---|---|---|---|---|---|
| (V-4) | CH₂–(dioxolane with CH₃, CH₃) | H | H | H | O | CH | OCH₃ | OCH₃ | $n_D^{24}$ 1.5249 |
| (V-5) | CH₂–(1,3-dioxolane) | H | H | H | O | CBr | OCH₃ | OCH₃ | |
| (V-6) | CH₂–(1,3-dioxolane) | H | H | H | S | CBr | OCH₃ | OCH₃ | |
| (V-7) | CH₂–(1,3-dioxolane) | H | H | H | O | COCH₃ | OCH₃ | OCH₃ | |
| (V-8) | CH₂–(1,3-dioxolane) | H | H | H | O | CH | OCH₃ | OCH₃ | $n_D^{21.5}$ 1.5408 |
| (V-9) | CH₂–(1,3-dioxolane) | CH₃ | H | H | O | CH | OCH₃ | OCH₃ | |
| (V-10) | CH₂–(1,3-dioxolane) | H | H | H | O | CH | OCH₃ | OCH₃ | $n_D^{22}$ 1.5367 |
| (V-11) | CH₂–(1,3-dioxolane) | H | H | F | O | CCl | OCH₃ | OCH₃ | |
| (V-12) | CH₂CH₂–(1,3-dioxane) | H | H | OCH₃ | O | CH | OCH₃ | OCH₃ | |
| (V-13) | CH₂CH₂–(1,3-dioxane) | H | H | F | O | CH | OCH₃ | OCH₃ | |
| (V-14) | CH₂CH₂–(1,3-dioxolane) | H | Cl | H | O | CH | OCH₃ | OCH₃ | m.p. 71–72° C. |

TABLE 1-continued

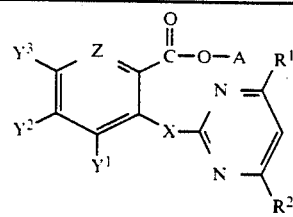

| Compound No. | A | $Y^1$ | $Y^2$ | $Y^3$ | X | Z | $R^1$ | $R^2$ | Physical properties (m.p., refractive index) |
|---|---|---|---|---|---|---|---|---|---|
| (V-15) | CH₂CH₂-⟨O-CH₂-CH₂-O⟩ | H | CH₃ | H | O | CH | OCH₃ | OCH₃ | m.p. 67–68° C. |
| (V-16) | CH₂CH₂-⟨O-CH₂-CH₂-CH₂-O⟩ | H | Cl | H | O | CH | OCH₃ | OCH₃ | $n_D^{24}$ 1.5285 |
| (V-17) | CH₂CH₂-⟨O-CH₂-CH₂-CH₂-O⟩ | H | CH₃ | H | O | CH | OCH₃ | OCH₃ | $n_D^{24}$ 1.5215 |
| (V-18) | CH₂CH₂-⟨O-CH₂-CH₂-CH₂-O⟩ | H | H | H | O | CH | CH₃ | CH₃ | $n_D^{24}$ 1.5419 |
| (V-19) | CH₂CH₂-⟨O-CH₂-CH₂-CH₂-O⟩ | H | H | H | O | CH | Cl | OCH₃ | $n_D^{24}$ 1.5375 |
| (V-20) | CH₂CH₂-⟨O-CH₂-CH₂-CH₂-O⟩ | H | H | H | O | N | OCH₃ | OCH₃ | $n_D^{24}$ 1.5193 |
| (V-21) | CH₂-⟨O-CH₂-CH₂-CH₂-O⟩ | H | H | H | O | N | OCH₃ | OCH₃ | $n_D^{24}$ 1.5055 |
| (V-22) | CH₂CH₂-⟨O-CH₂-CH₂-O⟩ | H | H | H | O | N | OCH₃ | OCH₃ | $n_D^{24}$ 1.5190 |
| (V-23) | CH₂CH₂-⟨O-CH₂-CH₂-CH₂-O⟩ | H | H | H | O | CCl | OCH₃ | OCH₃ | $n_D^{24}$ 1.5243 |
| (V-24) | CH₂CH₂-⟨O-CH₂-CH₂-CH₂-O⟩ | H | H | H | O | CF | OCH₃ | OCH₃ | |
| (V-25) | CH₂-⟨O-CH₂-CH₂-CH₂-O⟩ | H | H | H | O | CCl | OCH₃ | OCH₃ | |

TABLE 1-continued

Structure:
$Y^3$, Z, C(=O)—O—A on a vinyl group; $Y^2$, $Y^1$ on the chain; X linking to a pyrimidine with $R^1$ and $R^2$ substituents.

| Compound No. | A | $Y^1$ | $Y^2$ | $Y^3$ | X | Z | $R^1$ | $R^2$ | Physical properties (m.p., refractive index) |
|---|---|---|---|---|---|---|---|---|---|
| (V-26) | CH₂CH₂CH₂–(1,3-dioxane) | H | H | H | O | CCl | OCH₃ | OCH₃ | |
| (V-27) | CH₂CH₂–(1,3-dioxane) | H | H | F | O | CCl | OCH₃ | OCH₃ | |
| (V-28) | CH₂CH₂–(1,3-dioxane) | H | H | OCH₃ | O | CCl | OCH₃ | OCH₃ | |
| (V-29) | CH₂CH₂–(1,3-dioxane) | H | H | H | O | CBr | OCH₃ | OCH₃ | |
| (V-30) | CH₂CH₂–(1,3-dioxane) | H | H | H | S | CBr | OCH₃ | OCH₃ | |
| (V-31) | CH₂CH₂–(1,3-dioxane) | H | H | H | O | COCH₃ | OCH₃ | OCH₃ | |
| (V-32) | CH₂CH₂–(1,3-dioxane) | H | H | H | S | CCl | OCH₃ | OCH₃ | |
| (V-33) | CH₂CH₂–(1,3-dioxane) | H | H | H | O | CCF₃ | OCH₃ | OCH₃ | |
| (V-34) | CH₂CH₂–(1,3-dioxane) | H | H | H | O | CCH₃ | OCH₃ | OCH₃ | |
| (V-35) | CH₂CH₂–(1,3-dioxane) | H | H | H | O | CNO₂ | OCH₃ | OCH₃ | |

TABLE 1-continued

Structure:

Y³–C(Z)=C(–C(=O)–O–A)–... aryl ring with Y¹, Y² substituents; linked via X to a pyrimidine bearing R¹ and R².

| Compound No. | A | Y¹ | Y² | Y³ | X | Z | R¹ | R² | Physical properties (m.p., refractive index) |
|---|---|---|---|---|---|---|---|---|---|
| (V-36) | CH₂CH₂–CH(O–)(O–) (1,3-dioxane) | H | H | H | O | CNH₂ | OCH₃ | OCH₃ | |
| (V-37) | CH₂CH₂–CH(O–)(O–) | H | H | H | O | CCN | OCH₃ | OCH₃ | |
| (V-38) | CH₂CH₂–CH(O–)(O–) | H | H | H | O | CC₂H₅ | OCH₃ | OCH₃ | |
| (V-39) | CH₂CH₂–CH(O–)(O–) | H | H | H | O | COH | OCH₃ | OCH₃ | |
| (V-40) | CH₂CH₂–CH(O–)(O–) | H | H | H | O | CSCH₃ | OCH₃ | OCH₃ | |
| (V-41) | CH₂CH₂–CH(O–)(O–) | H | H | H | O | CCOOCH₃ | OCH₃ | OCH₃ | |
| (V-42) | CH₂CH₂–CH(O–)(O–) | H | H | H | O | CCON(CH₃)₂ | OCH₃ | OCH₃ | |
| (V-43) | CH₂CH₂–CH(O–)(O–) | H | H | H | O | COC₃H₇(i) | OCH₃ | OCH₃ | |
| (V-44) | CH₂CH₂–CH(O–)(O–) | H | H | H | O | CC₄H₉(n) | OCH₃ | OCH₃ | |
| (V-45) | CH₂CH₂–CH(O–)(O–) | H | H | H | O | COCF₂CHF₂ | OCH₃ | OCH₃ | |
| (V-46) | CH₂CH₂–CH(O–)(O–) | H | H | H | O | CSC₅H₁₁ | OCH₃ | OCH₃ | |

TABLE 1-continued

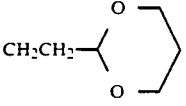

| Compound No. | A | Y¹ | Y² | Y³ | X | Z | R¹ | R² | Physical properties (m.p., refractive index) |
|---|---|---|---|---|---|---|---|---|---|
| (V-47) | CH₂CH₂-⟨dioxolane⟩ | H | H | H | O | CSOC₂H₅ | OCH₃ | OCH₃ | |
| (V-48) | CH₂CH₂-⟨dioxolane⟩ | H | H | H | O | CSO₂CH₃ | OCH₃ | OCH₃ | |
| (V-49) | CH₂CH₂-⟨dioxolane⟩ | H | H | H | O | C-C₆H₅ | OCH₃ | OCH₃ | |
| (V-50) | CH₂CH₂-⟨dioxolane⟩ | H | H | H | O | C-(2-CH₃)C₆H₄ | OCH₃ | OCH₃ | |
| (V-51) | CH₂CH₂-⟨dioxolane⟩ | H | H | H | O | C-(3-OCH₃)C₆H₄ | OCH₃ | OCH₃ | |
| (V-52) | CH₂CH₂-⟨dioxolane⟩ | H | H | H | O | C-(4-F)C₆H₄ | OCH₃ | OCH₃ | |
| (V-53) | CH₂CH₂-⟨dioxolane⟩ | H | H | H | O | C-(2-COOC₂H₅)C₆H₄ | OCH₃ | OCH₃ | |
| (V-54) | CH₂CH₂-⟨dioxolane⟩ | H | H | H | O | C-(3-CF₃)C₆H₄ | OCH₃ | OCH₃ | |
| (V-55) | CH₂CH₂-⟨dioxolane⟩ | H | H | H | O | C-(2,4-Cl₂)C₆H₃ | OCH₃ | OCH₃ | |
| (V-56) | CH₂CH₂-⟨dioxolane⟩ | H | H | H | O | C-(2,3-(C₂H₅)₂)C₆H₃ | OCH₃ | OCH₃ | |

TABLE 1-continued

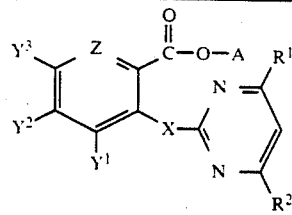

| Compound No. | A | Y¹ | Y² | Y³ | X | Z | R¹ | R² | Physical properties (m.p., refractive index) |
|---|---|---|---|---|---|---|---|---|---|
| (V-57) | CH₂CH₂—O—CH(CH₃)—O (1,3-dioxolane, 4-methyl) | H | H | H | O | CCl | OCH₃ | OCH₃ | |
| (V-58) | CH₂CH₂—O—C(CH₃)₂—O | H | H | H | O | CF | OCH₃ | OCH₃ | |
| (V-59) | CH₂CH₂—O—C(CH₃)(CH₃)—CH₂—O | H | H | H | O | CCl | OCH₃ | OCH₃ | |
| (V-60) | CH₂CH₂—O—C(C₃H₇(n))(CH₃)—CH₂—O | H | H | H | S | CCl | OCH₃ | OCH₃ | |
| (V-61) | CH₂CH₂—O—CH₂—CH(CH₃)—O | H | H | H | O | CBr | OCH₃ | OCH₃ | |
| (V-62) | CH₂CH₂—O—CH₂—C(CH₃)₂—O | H | H | H | S | CBr | OCH₃ | OCH₃ | |
| (V-63) | CH₂CH₂—O—CH₂—C(C₂H₅)(CH₃)—O | H | H | H | O | COCH₃ | OCH₃ | OCH₃ | |
| (V-64) | CH₂CH₂—O—CH₂—C(C₂H₅)(C₄H₉(n))—O | H | H | H | O | CCl | OCH₃ | OCH₃ | |

Production Examples for the compound (2), a starting material, are shown below.

PRODUCTION EXAMPLE 9

9.00 Grams of acetylsalycilic acid and 9.95 g of 2-(2-bromoethyl)-1,3-dioxane were dissolved in 100 ml of N,N-dimethylformaide was mixed with 7.60 g of anhydrous potassium carbonate. The resulting solution was stirred at 120° C. to 130° C. for 3 hours. The reaction solution was poured into diluted hydrochloric acid, and extracted with ethyl acetate. The organic layer separated from the aqueous layer was washed with saturated sodium chloride solution and dried over anhydrous magnesium sulfate The solvent was removed under reduced pressure, and the residue obtained was distilled under reduced pressure to obtain 10.5 g of 2-(1,3-dioxan-2-yl)ethyl salycilate in a yield of 83%.

b.p.: 120° C.–122° C./0.07 mmHg $n_D^{24}$ 1.5246

Table 2 illustrates specific examples of the compound (2), which can be produced by using the corresponding starting materials.

TABLE 2

[Structure: benzene ring with substituents Y³, Y², Y¹, XH, and Z-C(=O)-O-A]

| A | Y¹ | Y² | Y³ | X | Z |
|---|----|----|----|----|----|
| oxetanyl | H | H | H | O | CF |
| oxetanyl | H | H | H | O | CCl |
| tetrahydrofuranyl | H | H | H | O | CH |
| tetrahydrofuranyl | H | H | H | S | CCl |
| tetrahydrofuranyl | H | H | H | O | CBr |
| tetrahydrofuranyl | H | H | H | S | CBr |
| tetrahydropyranyl | H | H | H | O | COCH₃ |
| tetrahydropyranyl | H | H | H | O | CCl |
| tetrahydropyranyl | H | H | H | O | CCl |
| tetrahydropyranyl | H | H | H | O | CF |
| tetrahydropyranyl | H | H | H | O | N |
| oxepanyl | H | H | H | O | CCF₃ |

TABLE 2-continued
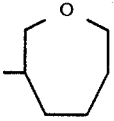
| A | Y¹ | Y² | Y³ | X | Z |
|---|----|----|----|---|---|
| 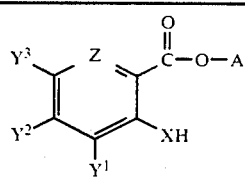 | H | H | H | O | CCH₃ |
| 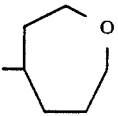 | H | H | H | O | CC₆H₅ |
| 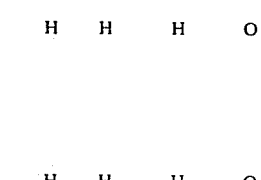 | H | H | H | O | CNO₂ |
| 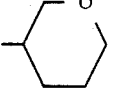 | H | H | H | O | CCl |
| 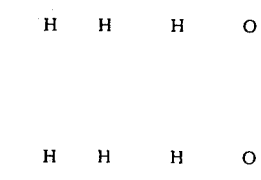 | H | H | H | O | N |
| 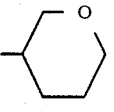 | H | H | H | O | CF |
| 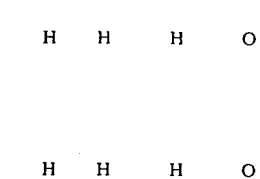 | H | H | H | O | CCl |
| 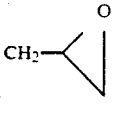 | H | H | H | S | CCl |
| 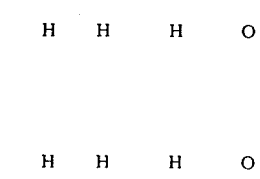 | H | H | H | O | CH |
| 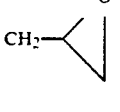 | H | H | H | S | CBr |
| 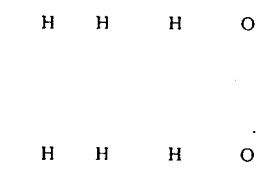 | H | H | H | O | CH |

TABLE 2-continued

[Structure: Y³, Z, C(=O)-O-A at top; Y², Y¹, XH on benzene ring]

| A | Y¹ | Y² | Y³ | X | Z |
|---|----|----|----|----|----|
| CH₂-(oxetanyl) | H | H | H | O | CCl |
| CH₂-(tetrahydrofuran-2-yl) | H | H | H | O | CH |
| CH₂-(tetrahydrofuran-3-yl) | H | H | H | O | CCF₃ |
| CH₂CH₂CH₂-(tetrahydrofuran-3-yl) | H | H | H | O | CSCH₃ |
| CH₂CH₂-(tetrahydropyran-2-yl) | H | H | H | O | CC₂H₅ |
| (CH₂)₅-(tetrahydropyran-3-yl) | H | H | H | O | CCN |
| CH₂CH₂-(tetrahydropyran-4-yl) | H | H | H | O | CNO₂ |
| CH₂-(2-methyloxiranyl) | H | H | H | O | COCH₃ |
| CH₂-(2,2-dimethyloxiranyl) | H | H | H | O | COH |
| -(1,3-dioxan-4-yl)methyl | H | H | H | O | N |
| -(1,3-dioxan-4-yl)methyl | Cl | H | H | O | CF |

TABLE 2-continued

Structure:
$$Y^3-C(Z)=C(-C(=O)-O-A)-C(XH)=C(Y^1)-C(Y^2)=$$
(benzene ring with substituents: Y³, Z, COOA, XH, Y¹, Y²)

| A | Y¹ | Y² | Y³ | X | Z |
|---|----|----|----|---|---|
| 1,3-dioxane-5-yl | H | CH₃ | H | O | CCl |
| 1,3-dioxane-5-yl | H | H | OCH₃ | S | CCl |
| 1,3-dioxane-5-yl | H | H | F | O | CBr |
| 1,3-dioxane-5-yl | C₂H₅ | H | H | S | CBr |
| 1,3-dioxane-5-yl | H | Cl | H | O | COCH₃ |
| 1,3-dioxane-5-yl | H | H | F | O | CCF₃ |
| 1,3-dioxepane-5-yl | H | H | H | O | CCl |
| 2,2-dimethyl-1,3-dioxepane-5-yl | H | H | H | O | CF |
| 1,3-dioxane-5-yl | H | H | H | O | CH |
| 2,2-dimethyl-1,3-dioxane-5-yl | H | H | H | S | CCl |
| 2,2-dimethyl-1,3-dioxane-5-yl | Cl | H | H | O | CBr |

TABLE 2-continued

Structure:
$$Y^3\text{-CH=C(Z)-C(=O)-O-A}$$
with $Y^2$, $Y^1$, and XH substituents on the diene chain

| A | $Y^1$ | $Y^2$ | $Y^3$ | X | Z |
|---|---|---|---|---|---|
| -CH₂-C(CH₃)(C₂H₅)(OCH₂-)(OCH₂-) [1,3-dioxane with CH₃, C₂H₅] | H | H | H | S | CBr |
| -CH₂-C(C₂H₅)(C₂H₅)(OCH₂-)(OCH₂-) | H | H | H | O | COCH₃ |
| -CH₂-C(C₂H₅)(C₃H₇(n))(OCH₂-)(OCH₂-) | H | H | H | O | CCl |
| -CH₂CH₂-(1,3-dioxan-2-yl) (6-membered) | H | H | H | O | CH |
| -CH₂CH₂-(1,3-dioxolan-2-yl) (5-membered) | H | H | H | O | CH |
| -CH₂-(1,3-dioxolan-2-yl) | H | H | H | O | CCl |
| -CH₂-(2,2-dimethyl-1,3-dioxolan-4-yl) | H | H | H | O | CH |
| -CH₂-(1,3-dioxolan-2-yl) | H | H | H | O | CBr |
| -CH₂-(1,3-dioxolan-2-yl) | H | H | H | S | CBr |
| -CH₂-(1,3-dioxolan-2-yl) | H | H | H | O | COCH₃ |
| -CH₂-(1,3-dioxolan-4-yl) | Cl | H | H | O | CH |

TABLE 2-continued

Structure: Y³ and Z on one ring carbon, Y² and Y¹ on adjacent carbons, with C(=O)—O—A and XH substituents:

$$\text{Y}^3\text{-C(Z)=C(-C(=O)-O-A)-C(XH)=C(Y}^1\text{)-C(Y}^2\text{)}$$

| A | Y¹ | Y² | Y³ | X | Z |
|---|---|---|---|---|---|
| CH₂—(1,3-dioxolan-2-yl) | CH₃ | H | H | O | CH |
| CH₂—(1,3-dioxolan-2-yl) | H | H | H | O | CH |
| CH₂—(1,3-dioxolan-2-yl) | H | H | F | O | CCl |
| CH₂CH₂—(1,3-dioxan-2-yl) | H | H | OCH₃ | O | CH |
| CH₂CH₂—(1,3-dioxan-2-yl) | H | H | F | O | CH |
| CH₂CH₂—(1,3-dioxan-2-yl) | H | Cl | H | O | CH |
| CH₂CH₂—(1,3-dioxan-2-yl) | H | CH₃ | H | O | CH |
| CH₂CH₂—(1,3-dioxan-2-yl) | H | Cl | H | O | CH |
| CH₂CH₂—(1,3-dioxan-2-yl) | H | CH₃ | H | O | CH |
| CH₂CH₂—(1,3-dioxan-2-yl) | H | H | H | O | N |
| CH₂—(1,3-dioxan-2-yl) | H | H | H | O | N |

TABLE 2-continued

[Structure: benzene ring with Y³ at top-left position, Z adjacent, C(=O)—O—A group, XH group, Y¹ at bottom, Y² at left]

| A | Y¹ | Y² | Y³ | X | Z |
|---|----|----|----|---|---|
| CH₂CH₂—(1,3-dioxolane) | H | H | H | O | N |
| CH₂CH₂—(1,3-dioxane) | H | H | H | O | CCl |
| CH₂CH₂—(1,3-dioxane) | H | H | H | O | CF |
| CH₂—(1,3-dioxane) | H | H | H | O | CCl |
| CH₂CH₂CH₂—(1,3-dioxane) | H | H | H | O | CCl |
| CH₂CH₂—(1,3-dioxane) | H | H | F | O | CCl |
| CH₂CH₂—(1,3-dioxane) | H | H | OCH₃ | O | CCl |
| CH₂CH₂—(1,3-dioxane) | H | H | H | O | CBr |
| CH₂CH₂—(1,3-dioxane) | H | H | H | S | CBr |
| CH₂CH₂—(1,3-dioxane) | H | H | H | O | COCH₃ |
| CH₂CH₂—(1,3-dioxane) | H | H | H | S | CCl |

TABLE 2-continued $$\text{structure with } Y^3, Z, C(=O)-O-A, Y^2, Y^1, XH$$

| A | Y¹ | Y² | Y³ | X | Z |
|---|---|---|---|---|---|
| CH₂CH₂-[O-/O-] (dioxane) | H | H | H | O | CCF₃ |
| CH₂CH₂-[O-/O-] | H | H | H | O | CCH₃ |
| CH₂CH₂-[O-/O-] | H | H | H | O | CNO₂ |
| CH₂CH₂-[O-/O-] | H | H | H | O | CNH₂ |
| CH₂CH₂-[O-/O-] | H | H | H | O | CCN |
| CH₂CH₂-[O-/O-] | H | H | H | O | CC₂H₅ |
| CH₂CH₂-[O-/O-] | H | H | H | O | COH |
| CH₂CH₂-[O-/O-] | H | H | H | O | CSCH₃ |
| CH₂CH₂-[O-/O-] | H | H | H | O | CCOOCH₃ |
| CH₂CH₂-[O-/O-] | H | H | H | O | CCON(CH₃)₂ |
| CH₂CH₂-[O-/O-] | H | H | H | O | COC₃H₇(i) |

TABLE 2-continued

Structure:
$$Y^3-\text{(ring)}-Z, \quad \text{with } C(=O)-O-A, \quad XH, \quad Y^1, Y^2$$

| A | Y¹ | Y² | Y³ | X | Z |
|---|---|---|---|---|---|
| CH₂CH₂–(1,3-dioxane) | H | H | H | O | CC₄H₉(n) |
| CH₂CH₂–(1,3-dioxane) | H | H | H | O | COCF₂CHF₂ |
| CH₂CH₂–(1,3-dioxane) | H | H | H | O | CSC₅H₁₁ |
| CH₂CH₂–(1,3-dioxane) | H | H | H | O | CSOC₂H₅ |
| CH₂CH₂–(1,3-dioxane) | H | H | H | O | CSO₂CH₃ |
| CH₂CH₂–(1,3-dioxane) | H | H | H | O | C–phenyl |
| CH₂CH₂–(1,3-dioxane) | H | H | H | O | C–(2-CH₃-phenyl) |
| CH₂CH₂–(1,3-dioxane) | H | H | H | O | C–(3-OCH₃-phenyl) |
| CH₂CH₂–(1,3-dioxane) | H | H | H | O | C–(4-F-phenyl) |
| CH₂CH₂–(1,3-dioxane) | H | H | H | O | C–(2-COOC₂H₅-phenyl) |
| CH₂CH₂–(1,3-dioxane) | H | H | H | O | C–(3-CF₃-phenyl) |

TABLE 2-continued
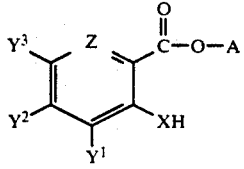
| A | Y¹ | Y² | Y³ | X | Z |
|---|---|---|---|---|---|
| 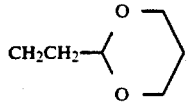 | H | H | H | O | 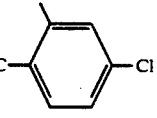 |
| 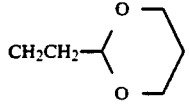 | H | H | H | O | 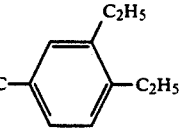 |
| 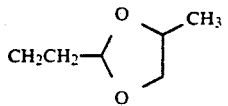 | H | H | H | O | CCl |
| 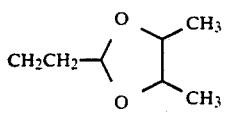 | H | H | H | O | CF |
| 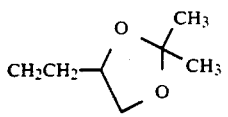 | H | H | H | O | CCl |
| 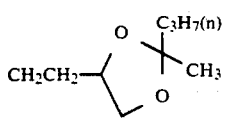 | H | H | H | S | CCl |
| 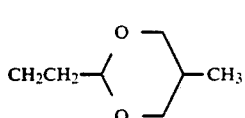 | H | H | H | O | CBr |
| 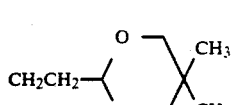 | H | H | H | S | CBr |
| 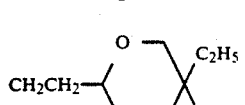 | H | H | H | O | COCH$_3$ |
| 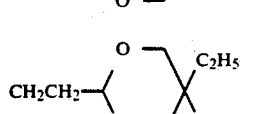 | H | H | H | O | CCl |
Formulation Examples are shown below. In the examples, the present compound (1) is shown by Compound No. in Table 3, and parts are by weight.
FORMULATION EXAMPLE 1
Fifty parts of any one of the present compounds (IV-11), (V-14) and (V-15), 3 parts of calcium lignosulfonate, 2 parts of sodium lauryl sulfate and 45 parts of synthetic hydrated silicon dioxide are well mixed while being powdered to obtain a wettable powder.

FORMULATION EXAMPLE 2

Ten parts of any one of the present compounds (V-1), (V-2), (II-3), (V-4), (III-5), (III-7), (V-8), (III-9), (V-10), (IV-11), (V-14), (V-15), (V-16), (V-17), (V-18), (V-19), (V-20), (V-21), (V-22) and (V-23), 14 parts of polyoxyethylene styrylphenyl ether, 6 parts of calcium dodecylbenzenesulfonate, 40 parts of xylene and 30 parts of cyclohexanone are well mixed to obtain an emulsifiable concentrate.

FORMULATION EXAMPLE 3

Two parts of any one of the present compounds (IV-11), (V-14) and (V-15), 1 part of synthetic hydrated silicon dioxide, 2 parts of calcium lignosulfonate, 30 parts of bentonite and 65 parts of kaolin clay are well pulverized and mixed. The resulting mixture is well kneaded with water, granulated and dried to obtain a granule.

FORMULATION EXAMPLE 4

Twenty five parts of any one of the present s (V-1), (V-2), (II-3), (V-4), (III-5), (III-7), (V-8), (III-9), (V-10), (IV-11), (V-14), (V-15), (V-16), (V-17), (V-18), (V-19), (V-20), (V-21), (V-22) and (V-23), 3 parts of polyoxyethylene sorbitan monooleate, 3 parts of CMC and 69 parts of water are mixed and wet- a pulverized until the particle size decreases to 5 microns or less. Thus, a suspension formulation is obtained.

That the present compounds are useful as an active ingredient for herbicides is shown by the following test examples In the examples, the present compound (1) is shown by Compound No. in Table 1, and compounds used for comparison are shown by Compound symbol in Table 3.

TABLE 3

| Compound symbol | Structural formula | Remarks |
|---|---|---|
| A | [structure: benzene ring with COOC$_2$H$_5$, CH$_3$, and O-C(=N-C(OCH$_3$)=CH-C(OCH$_3$)=N) substituents] | EP-0 249 708-A1 ($n_D^{23}$ 1.5271) |
| B | [structure: benzene ring with COOH, CH$_3$, and O-C(=N-C(OCH$_3$)=CH-C(OCH$_3$)=N) substituents] | EP-0 249 708-A1 (Compound No. 1) |
| C | [structure: benzene ring with COOCH$_3$ and O-C(=N-C(CH$_3$)=CH-C(OCH$_3$)=N) substituents] | EP-0 223 406-A1 (Compound No. 16) |
| D | [structure: benzene ring with COOC$_2$H$_5$ and O-C(=N-C(OCH$_3$)=CH-C(OCH$_3$)=N) substituents] | EP-0 223 406-A1 (Compound No. 18) |
| E | [structure: benzene ring with C(=O)-O-CH(CH$_3$)$_2$ and O-C(=N-C(OCH$_3$)=CH-C(OCH$_3$)=N) substituents] | EP-0 223 406-A1 (Compound No. 20) |

TABLE 3-continued

| Compound symbol | Structural formula | Remarks |
|---|---|---|
| F | [pyridine with C(=O)-O-CH(CH$_3$)$_2$ and O-pyrimidine(OCH$_3$)$_2$ substituent] | EP-0 249 707-A1 (Compound No. 4) |
| G | [pyridine with C(=O)OCH$_3$ and O-pyrimidine(OCH$_3$)$_2$ substituent] | EP-0 249 707-A1 (Compound No. 1) |
| H | [pyridine with C(=O)OH and O-pyrimidine(OCH$_3$)$_2$ substituent] | EP-0 249 707-A1 (Compound No. 8) |
| J | [benzene with C(=O)-O-CH$_2$CH$_2$CH(OC$_2$H$_5$)$_2$ and O-pyrimidine(OCH$_3$)$_2$ substituent] | Comparative Compound ($n_D^{24}$ 1.5129) |

The determination of the herbicidal activity and phytotoxicity was carried out as follows: When the states of emergence and growth of treated test plants (weeds and crops) at the time of determination were completely the same as or hardly different from those of untreated test plants, the value of determination was taken as "0". When the treated test plants were completely killed, or their emergence and growth were completely inhibited, the value of determination was taken as "5", and an interval between "0" and "5" was divided into four stages, i.e. "1", "2", "3" and "4". The evaluation was thus made in six stages

TEST EXAMPLE 1

Soil surface treatment test in upland field soil

Cylindrical plastic pots of 10 cm in diameter and 10 cm in depth were filled with upland field soil, and seeds of Japanese millet, oats, tall morningglory and velvetleaf were sowed in the respective pots and covered with soil. The test compounds were formulated into emulsifiable concentrates according to Formulation Example 2, and the prescribed amount of each emulsifiable concentrate was diluted with water corresponding to 10 liters-/are and uniformly applied onto the whole soil surface by means of an automatic sprayer. After application, the test plants were cultivated for 19 days in a greenhouse, and the herbicidal activity was examined. The results are shown in Table 4.

TABLE 4

| Test compound | Dosage rate of active ingredient (g/a) | Herbicidal activity | | | |
|---|---|---|---|---|---|
| | | Japanese millet | Oats | Tall morning-glory | Velvet-leaf |
| (V-1) | 5 | 5 | 5 | 4 | 4 |
| | 1.25 | 5 | 5 | 3 | 4 |
| (V-2) | 5 | 5 | 4 | 3 | 4 |
| | 1.25 | 5 | 4 | 3 | 4 |
| (II-3) | 5 | 5 | 4 | 3 | 4 |
| (V-4) | 5 | 5 | 4 | 3 | 4 |
| | 1.25 | 5 | 4 | 3 | 3 |
| (III-5) | 5 | 5 | 4 | 3 | 4 |
| | 1.25 | 5 | 4 | 3 | 4 |
| (III-7) | 5 | 5 | 4 | 4 | 4 |
| | 1.25 | 5 | 4 | 3 | 4 |
| (V-8) | 5 | 5 | 5 | 4 | 5 |
| | 1.25 | 5 | 4 | 3 | 4 |
| (III-9) | 5 | 5 | 4 | 3 | 4 |
| | 1.25 | 5 | 4 | 3 | 4 |
| (V-10) | 5 | 5 | 4 | 4 | 4 |
| | 1.25 | 5 | 4 | 3 | 3 |
| (IV-11) | 5 | 5 | 5 | 4 | 4 |

TABLE 4-continued

| Test compound | Dosage rate of active ingredient (g/a) | Herbicidal activity | | | |
|---|---|---|---|---|---|
| | | Japanese millet | Oats | Tall morning-glory | Velvet-leaf |
| A | 1.25 | 5 | 4 | 4 | 4 |
| | 5 | 4 | 3 | 0 | 1 |
| B | 1.25 | 2 | 1 | 0 | 0 |
| | 5 | 4 | 3 | 0 | 2 |
| C | 1.25 | 2 | 1 | 0 | 0 |
| | 5 | 3 | 3 | 0 | 1 |
| | 1.25 | 1 | 2 | 0 | 0 |

TEST EXAMPLE 2

Soil surface treatment test in upland field soil

Cylindrical plastic pots of 10 cm in diameter and 10 cm in depth were filled with upland field soil, and seeds of velvetleaf were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in Table 5.

TABLE 5

| Test compound | Dosage rate of active ingredient (g/a) | Herbicidal activity Velvetleaf |
|---|---|---|
| (V-17) | 5 | 4 |
| A | 5 | 1 |

TEST EXAMPLE 3

Soil surface treatment test in upland field soil

Cylindrical plastic pots of 10 cm in diameter and 10 cm in depth were filled with upland field soil, and seeds of Japanese millet, oats and velvetleaf were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in Table 6.

TABLE 6

| Test compound | Dosage rate of active ingredient (g/a) | Herbicidal activity | | |
|---|---|---|---|---|
| | | Japanese millet | Oats | Velvet-leaf |
| (V-19) | 5 | 4 | 4 | 3 |
| (V-20) | 5 | 4 | 4 | 4 |
| (V-21) | 5 | 4 | 4 | 4 |
| (V-22) | 5 | 5 | 4 | 4 |
| (V-23) | 5 | 4 | 3 | 3 |
| H | 5 | 2 | 1 | 3 |

TEST EXAMPLE 4

Soil surface treatment test in upland field soil

Cylindrical plastic pots of 10 cm in diameter and 10 cm in depth were filled with upland field soil, and seeds of Japanese millet were sowed in the respective pots and covered with soil. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 19 days in a greenhouse, and the herbicidal activity was examined. The results are shown in Table 7.

TABLE 7

| Test compound | Dosage rate of active ingredient (g/a) | Herbicidal activity Japanese millet |
|---|---|---|
| (III-7) | 0.31 | 4 |
| (V-10) | 0.31 | 4 |
| D | 0.31 | 3 |
| E | 0.31 | 1 |
| F | 0.31 | 2 |

TEST EXAMPLE 5

Foliar treatment test in upland field soil

Cylindrical plastic pots of 10 cm in diameter and 10 cm in depth were filled with upland field soil, and seeds of Japanese millet, oats, radish, velvetleaf and tall morningglory were sowed in the respective pots and cultivated for 8 days in a greenhouse.

Thereafter, the test compounds were formulated into emulsifiable concentrates according to Formulation Example 2, and the prescribed amount of each emulsifiable concentrate was diluted with a spreading agent-containing water corresponding to 10 liters/are and uniformly applied from above onto the whole foliar portion of the test plants by means of an automatic sprayer. After application, the test plants were cultivated for 19 days in a greenhouse, and the herbicidal activity was examined.

The results are shown in Table 8.

TABLE 8

| Test compound | Dosage rate of active ingredient (g/a) | Herbicidal activity | | | | |
|---|---|---|---|---|---|---|
| | | Japanese millet | Oats | Radish | Velvet-leaf | Tall morning glory |
| (V-1) | 5 | 5 | 5 | 4 | 5 | 4 |
| (V-2) | 5 | 5 | 4 | 4 | 5 | 4 |
| (II-3) | 5 | 4 | 5 | 4 | 3 | 3 |
| (V-4) | 5 | 5 | 4 | 4 | 5 | 5 |
| (III-5) | 5 | 4 | 4 | 3 | 5 | 3 |
| (III-7) | 5 | 5 | 4 | 4 | 4 | 4 |
| (V-8) | 5 | 5 | 5 | 4 | 5 | 4 |
| (III-9) | 5 | 5 | 4 | 4 | 4 | 4 |
| (V-10) | 5 | 5 | 5 | 4 | 5 | 4 |
| (IV-11) | 5 | 4 | 4 | 3 | 4 | 3 |
| A | 5 | 4 | 2 | 1 | 1 | 2 |
| B | 5 | 3 | 3 | 1 | 1 | 1 |
| C | 5 | 3 | 2 | 2 | 1 | 2 |

TEST EXAMPLE 6

Foliar treatment test in upland field soil

Cylindrical plastic pots of 10 cm in diameter and 10 cm in depth were filled with upland field soil, and seeds of Japanese millet, oats, radish and velvetleaf were sowed in the respective pots and cultivated for 8 days in a greenhouse.

Thereafter, the test compounds were formulated into emulsifiable concentrates according to Formulation Example 2, and the prescribed amount of each emulsifiable concentrate was diluted with a spreading agent-containing water corresponding to 10 liters/are and uniformly applied from above onto the whole foliar portion of the test plants by means of an automatic sprayer. After application, the test plants were cultivated for days in a greenhouse, and the herbicidal activity was examined.

The results are shown in Table 9.

TABLE 9

| Test compound | Dosage rate of active ingredient (g/a) | Herbicidal activity | | | |
|---|---|---|---|---|---|
| | | Japanese millet | Oats | Radish | Velvet-leaf |
| (V-19) | 5 | 4 | 4 | 3 | 4 |
| (V-20) | 5 | 5 | 5 | 5 | 5 |
| (V-21) | 5 | 5 | 5 | 5 | 5 |
| (V-22) | 5 | 5 | 5 | 5 | 5 |
| (V-23) | 5 | 4 | 3 | 5 | 5 |
| E | 5 | 2 | 2 | 2 | 2 |

TEST EXAMPLE 7

Foliar treatment test in upland field soil

Cylindrical plastic pots of 10 cm in diameter and 10 cm in depth were filled with upland field soil, and seeds of Japanese millet, oats and radish were sowed in the respective pots and cultivated for 8 days in a greenhouse.

Thereafter, the test compounds were formulated into emulsifiable concentrates according to Formulation Example 2, and the prescribed amount of each emulsifiable concentrate was diluted with a spreading agent-containing water corresponding to 10 liters/are and uniformly applied from above onto the whole foliar portion of the test plants by means of an automatic sprayer.

After application, the test plants were cultivated for days in a greenhouse, and the herbicidal activity was examined.

The results are shown in Table 10.

TABLE 10

| Test compound | Dosage rate of active ingredient (g/a) | Herbicidal activity | | |
|---|---|---|---|---|
| | | Japanese millet | Oats | Radish |
| (V-20) | 0.31 | 4 | 4 | 4 |
| (V-21) | 0.31 | 4 | 4 | 4 |
| (V-22) | 0.31 | 4 | 4 | 4 |
| F | 0.31 | 1 | 1 | 1 |
| J | 0.31 | 2 | 2 | 2 |

TEST EXAMPLE 8

Foliar treatment test in upland field soil

Cylindrical plastic pots of 10 cm in diameter and 10 cm in depth were filled with upland field soil, and seeds of Japanese millet were sowed in the respective pots and cultivated for 8 days in a greenhouse.

Thereafter, the test compounds were formulated into emulsifiable concentrates according to Formulation Example 2, and the prescribed amount of each emulsifiable concentrate was diluted with a spreading agent-containing water corresponding to 10 liters/are and uniformly applied from above onto the whole foliar portion of the test plants by means of an automatic sprayer. After application, the test plants were cultivated for 19 days in a greenhouse, and the herbicidal activity was examined.

The results are shown in Table 11.

TABLE 11

| Test compound | Dosage rate of active ingredient (g/a) | Herbicidal activity Japanese millet |
|---|---|---|
| (V-10) | 0.08 | 4 |
| D | 0.08 | 2 |
| G | 0.08 | 2 |

TEST EXAMPLE 9

Soil treatment test in upland field soil

Vats of 33×23 cm$^2$ in area and 11 cm in depth were filled with upland field soil, and seeds of soybean, cotton, corn, velvetleaf, black nightshade, barnyardgrass, giant foxtail and johnsongrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to liters-/are and uniformly applied onto the whole soil surface by means of an automatic sprayer.

After application, the test plants were cultivated for 18 days in a greenhouse, and the herbicidal activity and phytotoxicity were examined. The results ar shown in Table 12.

TABLE 12

| Test compound | Dosage rate of active ingredient (g/a) | Phytotoxicity | | | Herbicidal activity | | | | |
|---|---|---|---|---|---|---|---|---|---|
| | | Soy-bean | Cotton | Corn | Velvet-leaf | Black nightshade | Barnyard-grass | Green foxtail | Johnson-grass |
| (V-1) | 5 | 1 | 0 | 1 | 4 | 5 | 5 | 5 | 4 |
|  | 1.25 | 1 | 0 | 0 | 3 | 5 | 4 | 4 | 4 |
| (II-3) | 5 | 0 | 0 | 0 | 4 | 4 | 4 | 4 | 4 |
|  | 1.25 | 0 | 0 | 0 | 3 | 4 | 3 | 3 | 3 |
| (III-5) | 5 | 0 | 0 | 1 | 3 | 4 | 4 | 4 | 4 |
| (III-7) | 5 | 1 | 1 | 1 | 3 | 4 | 4 | 4 | 5 |
| (V-8) | 5 | 1 | 1 | 1 | 4 | 5 | 5 | 4 | 4 |
| (III-9) | 5 | 0 | 1 | 1 | 3 | 4 | 4 | 4 | 4 |

TABLE 12-continued

| Test compound | Dosage rate of active ingredient (g/a) | Phytotoxicity Soybean | Cotton | Corn | Herbicidal activity Velvetleaf | Black nightshade | Barnyardgrass | Green foxtail | Johnsongrass |
|---|---|---|---|---|---|---|---|---|---|
| A | 5 | 2 | 2 | 0 | 0 | 0 | 2 | 1 | 3 |
|   | 1.25 | 0 | 2 | 0 | 0 | 0 | 1 | 0 | 2 |
| C | 5 | 0 | 0 | 0 | 0 | 0 | 1 | 1 | 0 |
|   | 1.25 | 0 | 0 | 0 | 0 | 0 | 1 | 1 | 0 |
| H | 5 | 0 | 0 | 0 | 2 | 2 | 0 | 1 | 0 |

TEST EXAMPLE 10

Soil treatment test in upland field soil

Vats of 33×23 cm² in area and 11 cm in depth were filled with upland field soil, and seeds of cotton, black nightshade and sicklepod were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined. The results are shown in Table 13.

TABLE 13

| Test compound | Dosage rate of active ingredient (g/a) | Phytotoxicity Cotton | Herbicidal activity Black nightshade | Sicklepod |
|---|---|---|---|---|
| (V-23) | 5 | 0 | 5 | 4 |
| D | 5 | 3 | 4 | 0 |
| H | 5 | 0 | 2 | 1 |

TEST EXAMPLE 11

Soil treatment test in upland field soil

Vats of 33×23 cm² in area and 11 cm in depth were filled with upland field soil, and seeds of soybean, cotton, corn, back nightshade and johnsongrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined. The results are shown in Table 14.

TABLE 14

| Test compound | Dosage rate of active ingredient (g/a) | Phytotoxicity Soybean | Cotton | Corn | Herbicidal activity Black nightshade | Johnsongrass |
|---|---|---|---|---|---|---|
| (V-21) | 2.5 | 0 | 1 | 0 | 4 | 4 |
| A | 2.5 | 1 | 2 | 0 | 0 | 3 |
| B | 2.5 | 0 | 0 | 0 | 0 | 2 |
| C | 2.5 | 0 | 0 | 0 | 0 | 0 |

TEST EXAMPLE 12

Soil treatment test in upland field soil

Vats of 33×23 cm² in area and 11 cm in depth were filled with upland field soil, and seeds of cotton, back nightshade, barnyardgrass, giant foxtail and johnsongrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined. The results are shown in Table 15.

TABLE 15

| Test compound | Dosage rate of active ingredient (g/a) | Phytotoxicity Cotton | Herbicidal activity Black nightshade | Barnyardgrass | Giant foxtail | Johnsongrass |
|---|---|---|---|---|---|---|
| (V-4) | 5 | 0 | 4 | 4 | 4 | 4 |
| (IV-11) | 5 | 0 | 4 | 4 | 4 | 4 |
| A | 5 | 2 | 0 | 2 | 1 | 3 |
| C | 5 | 0 | 0 | 1 | 1 | 0 |

TEST EXAMPLE 13

Soil treatment test in upland field soil

Vats of 33×23 cm² in area and 11 cm in depth were filled with upland field soil, and seeds of soybean, black nightshade and giant foxtail were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined. The results are shown in Table 16.

TABLE 16

| Test compound | Dosage rate of active ingredient (g/a) | Phytotoxicity Soybean | Herbicidal activity Black nightshade | Giant foxtail |
|---|---|---|---|---|
| (V-2) | 5 | 1 | 4 | 5 |
| (V-10) | 5 | 1 | 4 | 4 |
| (V-18) | 5 | 0 | 4 | 3 |
| (V-19) | 5 | 0 | 4 | 3 |
| (V-20) | 5 | 1 | 4 | 3 |
| (V-21) | 5 | 0 | 4 | 4 |

TABLE 16-continued

| Test compound | Dosage rate of active ingredient (g/a) | Phyto-toxicity Soybean | Herbicidal activity Black nightshade | Giant foxtail |
| --- | --- | --- | --- | --- |
| (V-22) | 5 | 1 | 4 | 4 |
| B | 5 | 0 | 0 | 3 |
| H | 5 | 0 | 2 | 1 |

TEST EXAMPLE 15

Soil treatment test in upland field soil

Vats of 33×23 cm² in area and 11 cm in depth were filled with upland field soil, and seeds of soybean, barnyardgrass, giant foxtail and johnsongrass were sowed in the respective vats and covered with soil in a thickness of 1 to 2 cm. The test compounds were formulated into emulsifiable concentrates according t Formulation Example 2, and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined. The results are shown in Table 17.

TABLE 17

| Test compound | Dosage rate of active ingredient (g/a) | Phyto-toxicity Soybean | Herbicidal activity Barnardgrass | Giant foxtail | Johnsongrass |
| --- | --- | --- | --- | --- | --- |
| (IV-11) | 2.5 | 0 | 3 | 4 | 3 |
| F | 2.5 | 1 | 0 | 2 | 2 |

TEST EXAMPLE 15

Soil treatment test in upland field soil

Vats of 33×23 cm² in area and 11 cm in depth were filled with upland field soil, and seeds of corn, black nightshade and giant foxtail were sowed in the respective vats and covered with soil in a thickness of 1 to 2 cm. The test compounds were formulated into emulsifiable concentrates according to Formulation Example 2 and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined. The results are shown in Table 18.

TABLE 18

| Test compound | Dosage rate of active ingredient (g/a) | Phyto-toxicity Corn | Herbicidal activity Black nightshade | Giant foxtail |
| --- | --- | --- | --- | --- |
| (V-22) | 5 | 0 | 4 | 4 |
| A | 5 | 0 | 0 | 1 |

TEST EXAMPLE 16

Soil treatment test in upland field soil

Vats of 33×23 cm² in area and 11 cm in depth were filled with upland field soil, and seeds of soybean, cotton, corn, giant foxtail and johnsongrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer.

After application, the test plants were cultivated for 18 days in a greenhouse, and the herbicidal activity and phytotoxicity were examined.

The results are shown in Table 19.

TABLE 19

| Test compound | Dosage rate of active ingredient (g/a) | Phytotoxicity Soybean | Cotton | Corn | Herbicidal activity Giant foxtail | Johnsongrass |
| --- | --- | --- | --- | --- | --- | --- |
| (V-1) | 0.63 | 0 | 0 | 0 | 4 | 4 |
| E | 0.63 | 0 | 0 | 0 | 2 | 2 |

TEST EXAMPLE 17

Foliar treatment test in upland field soil

Vats of 33×23 cm² in area and 11 cm in depth were filled with upland field soil, and seeds of cotton, corn, tall morningglory, velvetleaf, black nightshade, sicklepod, barnyardgrass, giant foxtail and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crops at that time varied depending upon the kind of the test plants, but the test plants were in the 0 5- to 4-leaf stage and were 5 to 30 cm in height. Eighteen days after application, the herbicidal activity and phytotoxicity were examined. The results are shown in Table 20. This test was carried out in a greenhouse through the whole test period.

TABLE 20

| Test compound | Dosage rate of active ingredient (g/a) | Phytotoxicity Cotton | Corn | Herbicidal activity Tall morningglory | Velvetleaf | Black nightshade | Sicklepod | Barnyardgrass | Giant foxtail | Johnsongrass |
| --- | --- | --- | --- | --- | --- | --- | --- | --- | --- | --- |
| (V-1) | 1.25 | 1 | 0 | 4 | 5 | 5 | 4 | 4 | 4 | 4 |
|  | 0.31 | 1 | 0 | 4 | 4 | 5 | 3 | 4 | 4 | 4 |
| (V-2) | 0.31 | 1 | 1 | 3 | 4 | 5 | 4 | 3 | 4 | 4 |
| (III-5) | 1.25 | 1 | 0 | 4 | 5 | 5 | 5 | 4 | 4 | 4 |
| (III-7) | 1.25 | 1 | 1 | 3 | 4 | 5 | 3 | 5 | 3 | 5 |
| (III-9) | 1.25 | 1 | 0 | 4 | 4 | 4 | 4 | 4 | 4 | 5 |
|  | 0.31 | 1 | 0 | 4 | 4 | 4 | 3 | 4 | 4 | 5 |
| (V-10) | 1.25 | 1 | 1 | 3 | 5 | 5 | 4 | 4 | 5 | 5 |

TABLE 20-continued

| Test compound | Dosage rate of active ingredient (g/a) | Phytotoxicity Cotton | Phytotoxicity Corn | Tall morningglory | Velvetleaf | Black nightshade | Sicklepod | Barnyardgrass | Giant foxtail | Johnsongrass |
|---|---|---|---|---|---|---|---|---|---|---|
| A | 1.25 | 0 | 0 | 0 | 0 | 4 | 1 | 2 | 0 | 2 |
|   | 0.31 | 0 | 0 | 0 | 0 | 3 | 0 | 1 | 0 | 0 |
| B | 1.25 | 0 | 0 | 0 | 1 | 3 | 2 | 1 | 0 | 1 |
|   | 0.31 | 0 | 0 | 0 | 1 | 3 | 1 | 0 | 0 | 0 |
| D | 1.25 | 2 | 2 | 0 | 1 | 2 | 0 | 2 | 0 | 3 |
|   | 0.31 | 1 | 0 | 0 | 0 | 2 | 0 | 2 | 0 | 3 |

TEST EXAMPLE 10

Foliar treatment test in upland field soil

Vats of 33×23 cm² in area and 11 cm in depth were filled with upland field soil, and seeds of cotton, tall morningglory, sicklepod, giant foxtail and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied depending upon the kind of the test plants, but the test plants were in the 0.5- to 2.5-leaf stage and were 5 to 15 cm in height. Eighteen days after application, the herbicidal activity and phytotoxicity were examined. The results are shown in Table 21. This test was carried out in a greenhouse through the whole test period.

TABLE 21

| Test compound | Dosage rate of active ingredient (g/a) | Phytotoxicity Cotton | Tall morningglory | Sicklepod | Giant foxtail | Johnsongrass |
|---|---|---|---|---|---|---|
| (V-1) | 1.25 | 1 | 4 | 4 | 4 | 4 |
| (III-9) | 1.25 | 1 | 4 | 4 | 4 | 5 |
| F | 1.25 | 2 | 3 | 3 | 1 | 3 |

TEST EXAMPLE 19

Foliar treatment test in upland field soil

Vats of 33×23 cm² in area and 11 cm in depth were filled with upland field soil, and seeds of velvetleaf, barnyardgrass, giant foxtail and johnsongrass were sowed in the respective vats and cultivated for 16 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds at that time varied depending upon the kind of the test plants, but the test plants were in the 1- to 2.5-leaf stage and were 5 to 15 cm in height. Eighteen days after application, the herbicidal activity was examined. The results are shown in Table 22. This test was carried out in a greenhouse through the whole test period.

TABLE 22

| Test compound | Dosage rate of active ingredient (g/a) | Velvetleaf | Barnyardgrass | Giant foxtail | Johnsongrass |
|---|---|---|---|---|---|
| (II-3) | 5 | 5 | 5 | 5 | 5 |
| A | 5 | 0 | 2 | 0 | 2 |

TEST EXAMPLE 20

Soil treatment test in upland field soil

Vats of 33×23 cm² in area and 11 cm in depth were filled with upland field soil, and seeds of wheat, pale smartweed, cleavers, chickweed, birdseye speedwell, field pansy, downy brome, wild oat, blackgrass and annual bluegrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in Table 23.

TABLE 23

| Test compound | Dosage rate of active ingredient (g/a) | Phytotoxicity Wheat | Pale smartweed | Cleavers | Chickweed | Birdseye speedwell | Field pansy | Downy brome | Wild oat | Blackgrass | Annual bluegrass |
|---|---|---|---|---|---|---|---|---|---|---|---|
| (V-4) | 5 | 0 | 4 | 5 | 4 | 4 | 3 | 4 | 4 | 4 | 4 |
|   | 1.25 | 0 | 4 | 3 | 3 | 4 | 3 | 4 | 3 | 4 | 4 |
| (III-9) | 5 | 0 | 4 | 3 | 4 | 4 | 4 | 5 | 4 | 4 | 4 |
|   | 1.25 | 0 | 4 | 3 | 3 | 4 | 3 | 4 | 4 | 3 | 4 |
| (IV-11) | 5 | 0 | 4 | 3 | 4 | 5 | 4 | 5 | 4 | 4 | 4 |
|   | 1.25 | 0 | 4 | 3 | 3 | 5 | 3 | 5 | 4 | 3 | 4 |
| A | 5 | 3 | 2 | 2 | 0 | 3 | 0 | 0 | 2 | 3 | 3 |
|   | 1.25 | 1 | 0 | 0 | 0 | 0 | 0 | 0 | 0 | 2 | 3 |
| B | 5 | 4 | 4 | 3 | 4 | 4 | 3 | 0 | 4 | 4 | 3 |
|   | 1.25 | 1 | 2 | 3 | 3 | 3 | 0 | 0 | 2 | 2 | 3 |
| C | 5 | 1 | 0 | 1 | 1 | 2 | 1 | 2 | 3 | 3 | 3 |
|   | 1.25 | 0 | 0 | 0 | 0 | 1 | 0 | 0 | 1 | 1 | 2 |

TEST EXAMPLE 21

Soil treatment test in upland field soil

Vats of 33×23 cm² in area and 11 cm in depth were filled with upland field soil, and seeds of beet, pale smartweed, downy brome and annual bluegrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in Table 24.

TABLE 24

| Test compound | Dosage rate of active ingredient (g/a) | Phytotoxicity Beet | Herbicidal activity Pale smartweed | Down brome | Annual bluegrass |
| --- | --- | --- | --- | --- | --- |
| (IV-11) | 1.25 | 1 | 4 | 5 | 4 |
| (V-22) | 0.63 | 1 | 4 | 4 | 4 |
| H | 2.5 | 3 | 1 | 2 | 3 |

TEST EXAMPLE 22

Soil treatment test in upland field soil

Vats of 33×23 cm² in area and 11 cm in depth were filled with upland field soil, and seeds of wheat and annual bluegrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in Table 25.

TABLE 25

| Test compound | Dosage rate of active ingredient (g/a) | Phytotoxicity Wheat | Herbicidal activity Annual bluegrass |
| --- | --- | --- | --- |
| (V-2) | 0.31 | 0 | 4 |
| (III-7) | 0.31 | 0 | 4 |
| (V-8) | 0.31 | 0 | 4 |
| G | 0.31 | 2 | 0 |

TEST EXAMPLE 23

Soil treatment test in upland field soil

Vats of 33×23 cm² in area and 11 cm in depth were filled with upland field soil, and seeds of wheat, birdseye speedwell, downy brome and annual bluegrass were sowed in the respective vats and covered with soil in a thickness of 1 to 2 cm. The test compounds were formulated into emulsifiable concentrates according to Formulation Example 2, and the prescribed amount of each emulsifiable concentrate was diluted with water corresponding to 10 liters/are and uniformly applied onto the whole soil surface by means of an automatic sprayer. After application, the test plants were cultivated for 25 days in a greenhouse, and the herbicidal activity and phytotoxicity were examined. The results are shown in Table 26.

TABLE 26

| Test compound | Dosage rate of active ingredient (g/a) | Phytotoxicity Wheat | Herbicidal activity Birdseye speedwell | Downy brome | Annual bluegrass |
| --- | --- | --- | --- | --- | --- |
| (III-5) | 1.25 | 0 | 4 | 4 | 4 |
| (V-8) | 1.25 | 0 | 4 | 4 | 4 |
| (V-19) | 2.5 | 0 | 4 | 4 | 4 |
| B | 5 | 4 | 4 | 0 | 3 |
|  | 1.25 | 1 | 3 | 0 | 3 |

TEST EXAMPLE 24

Foliar treatment test in upland field soil

Vats of 33×23 cm² in area and 11 cm in depth were filled with upland field soil, and seeds of pale smartweed, cleavers, chickweed, birdseye speedwell, field pansy, downy brome, wild oat, blackgrass and annual bluegrass were sowed in the respective vats and cultivated for 31 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds at that time varied depending upon the kind of the test plants, but the test plants were in the 1- to 4 leaf stage and were 3 to 25 cm in height. Twenty-five days after application, the herbicidal activity was examined. The results are shown in Table 27. This test was carried out in a greenhouse through the whole test period.

TABLE 27

| Test compound | Dosage rate of active ingredient (g/a) | Herbicidal activity | | | | | | | | |
| --- | --- | --- | --- | --- | --- | --- | --- | --- | --- | --- |
| | | Pale smartweed | Cleavers | Chickweed | Birdseye speedwell | Field pansy | Downy brome | Wild oat | Black grass | Annual bluegrass |
| (V-1) | 2.5 | 5 | 4 | 4 | 5 | 5 | 4 | 4 | 5 | 5 |
| (V-4) | 2.5 | 4 | 4 | 3 | 4 | 4 | 4 | 3 | 4 | 4 |
| (V-8) | 2.5 | 5 | 4 | 3 | 4 | 4 | 4 | 4 | 4 | 4 |
| (III-9) | 2.5 | 4 | 4 | 4 | 4 | 3 | 4 | 4 | 4 | 4 |
| A | 2.5 | 2 | 3 | 1 | 3 | 0 | 3 | 3 | 3 | 3 |
| B | 2.5 | 3 | 0 | 1 | 3 | 0 | 3 | 3 | 3 | 2 |
| C | 2.5 | 0 | 1 | 1 | 0 | 0 | 0 | 0 | 1 | 0 |

TEST EXAMPLE 25

Foliar treatment test in upland field soil

Vats of 33×23 cm² in area and 11 cm in depth were filled with upland field soil, and seeds of pale smartweed, chickweed, birdseye speedwell, field pansy, downy brome, wild oat, blackgrass and annual bluegrass were sowed in the respective vats and cultivated for 31 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds at that time varied depending upon the kind of the test plants, but the test plants were in the 1- to 4-leaf stage and were 3 to 25 cm in height. Twenty-five days after application, the herbicidal activity was examined. The results are shown in Table 28. This test was carried out in a greenhouse through the whole test period.

TABLE 28

| Test compound | Dosage rate of active ingredient (g/a) | Herbicidal activity | | | | | | | |
|---|---|---|---|---|---|---|---|---|---|
| | | Pale smartweed | Chickweed | Birdseye speedwell | Field pansy | Downy brome | Wild oat | Blackgrass | Annual bluegrass |
| (V-21) | 0.16 | 5 | 5 | 4 | 5 | 4 | 4 | 4 | 4 |
| (V-22) | 0.16 | 4 | 5 | 5 | 5 | 4 | 4 | 4 | 3 |
| F | 0.16 | 3 | 3 | 3 | 3 | 0 | 1 | 1 | 2 |
| J | 0.16 | 1 | 0 | 2 | 2 | 2 | 1 | 1 | 2 |

TEST EXAMPLE 26

Foliar treatment test in upland field soil

Vats of 33×23 cm² in area and 11 cm in depth were filled with upland field soil, and seeds of wheat, pale smartweed, cleavers, downy brome and annual bluegrass were sowed in the respective vats and cultivated for 31 days. Thereafter, the test compounds were formulated into emulsifiable concentrates according to Formulation Example 2, and the prescribed amount of each emulsifiable concentrate was diluted with water corresponding to 10 liters/are and uniformly applied from above onto the whole foliar portion of the test plants by means of an automatic sprayer. The conditions of growth of the weeds and crop at that time varied depending upon the kind of the test plants, but the test plants were in the 2- to 4-leaf stage and were 5 to 25 cm in height. Twenty-five days after application, the herbicidal activity and phytotoxicity were examined. The results are shown in Table 29. This test was carried out in a greenhouse through the whole test period.

TABLE 29

| Test compound | Dosage rate of active ingredient (g/a) | Phytotoxicity Wheat | Herbicidal activity | | | |
|---|---|---|---|---|---|---|
| | | | Pale smartweed | Cleavers | Downy brome | Annual bluegrass |
| (V-1) | 0.31 | 1 | 4 | 4 | 4 | 4 |
| (V-4) | 0.63 | 1 | 4 | 3 | 4 | 4 |
| H | 0.63 | 2 | 3 | 1 | 1 | 2 |
| J | 0.63 | 2 | 3 | 3 | 3 | 2 |

TEST EXAMPLE 27

Flooding treatment test in paddy field

Cylindrical plastic pots of 8 cm in diameter and 12 cm in depth were filled with paddy field soil, and seeds of barnyardgrass and bulrush were sowed 1 to 2 cm deep under the soil surface. After creating a state of paddy field by flooding, a tuber of arrowhead was buried 1 to 2 cm deep under the soil surface and cultivated in a greenhouse. After 6 days (at the initial stage of generation of every weed), the test compounds were formulated into emulsifiable concentrates according to Formulation Example 2, and the prescribed amount of each emulsifiable concentrate was diluted with 2.5 ml of water and applied onto the water surface. After application, the test plants were cultivated for 19 days in a greenhouse, and the herbicidal activity was examined. The results are shown in Table 30.

TABLE 30

| Test compound | Dosage rate of active ingredient (g/a) | Herbicidal activity | | |
|---|---|---|---|---|
| | | Barnyard grass | Bulrush | Arrowhead |
| (V-1) | 0.63 | 5 | 5 | 3 |
| (V-2) | 0.63 | 5 | 3 | 4 |
| (I-6) | 0.63 | 5 | 3 | 3 |
| (V-8) | 0.63 | 4 | 3 | 4 |
| (III-9) | 0.63 | 4 | 4 | 4 |
| (V-10) | 0.63 | 4 | 3 | 4 |
| (IV-11) | 0.63 | 5 | 3 | 3 |
| A | 0.63 | 4 | 1 | 3 |
| B | 0.63 | 2 | 0 | 3 |
| C | 0.63 | 3 | 0 | 3 |
| E | 0.63 | 1 | 0 | 1 |
| F | 0.63 | 2 | 2 | 2 |
| G | 0.63 | 2 | 1 | 2 |

TEST EXAMPLE 28

Flooding treatment test in paddy field

Wager's pots of 200 cm² were filled with paddy field soil, and seeds of barnyardgrass and broadleaf weeds (i.e. false pimpernel, indian toothcup, water wort and red stem [Ammannia spp.]) were sowed 1 to 2 cm deep under the soil surface. After creating a state of paddy field by water flooding, tubers of arrowhead and water nutgrass were buried 1 to 2 cm deep under the soil surface. Also rice seedlings of 2-leaf stage were transplanted into the pots. The weeds and crops were cultivated in a greenhouse. After 4 days (at the initial stage of germination of barnyardgrass), the test compounds were formulated into emulsifiable concentrates according to Formulation Example 2, a prescribed amount of each of the emulsifiable concentrates was diluted with 10 ml of water and applied onto the water surface in the pots. Water leakage decreasing the depth of flooding water by 3 cm was carried out on the day subsequent to and two days after the application of test compounds. The depth of flooding water in each pot was recovered and kept at 4 cm, while the test plants were cultivated for 20 days in a greenhouse. Then, the herbicidal activity and phytotoxicity was examined. The results are shown in Table 31.

TABLE 31

| Test compound | Dosage rate of active ingredient (g/a) | Phytotoxicity Rice | Herbicidal activity | | | |
|---|---|---|---|---|---|---|
| | | | Barnyard grass | Broadleaf weeds | Arrowhead | Water nutgrass |
| (V-4) | 0.16 | 0 | 4 | 4 | 4 | 4 |
| (III-7) | 0.16 | 0 | 3 | 5 | 3 | 3 |
| A | 0.16 | 0 | 0 | 0 | 1 | 0 |
| B | 0.16 | 0 | 0 | 0 | 0 | 0 |
| C | 0.16 | 0 | 0 | 0 | 0 | 0 |

TEST EXAMPLE 29

Flooding treatment test in paddy field

Wager's pots of 200 cm² were filled with paddy field soil, and seeds of barnyardgrass and broadleaf weeds (i.e. false pimpernel, indian toothcup, water wort and red stem [Ammannia spp.]) were sowed 1 to 2 cm deep under the soil surface. After creating a state of paddy field by water flooding, tubers of arrowhead and water nutgrass were buried 1 to 2 cm deep under the soil surface. The weeds were cultivated in a greenhouse. After 11 days (at the 2-leaf stage of barnyardgrass), the test compounds were formulated into emulsifiable concentrates according to Formulation Example 2, a prescribed amount of each of the emulsifiable concentrates was diluted with 10 ml of water and applied onto the water surface in the pots. Water leakage decreasing the depth of flooding water by 3 cm was carried out on the day subsequent to and two days after the application of test compounds. The depth of flooding water in each pot was recovered and kept at 4 cm, while the test plants were cultivated for 20 days in a greenhouse. Then, the herbicidal activity was examined. The results are shown in Table 32.

TABLE 32

| Test compound | Dosage rate of active ingredient (g/a) | Herbicidal activity | | | |
|---|---|---|---|---|---|
| | | Barnyard grass | Broadleaf weeds | Arrowhead | Water nutgrass |
| (V-1) | 0.63 | 4 | 3 | 3 | 4 |
| (V-4) | 0.63 | 5 | 4 | 4 | 3 |
| (III-7) | 0.63 | 4 | 4 | 3 | 3 |
| (III-9) | 0.63 | 4 | 3 | 4 | 3 |
| A | 0.63 | 1 | 0 | 2 | 0 |
| C | 0.63 | 0 | 0 | 0 | 0 |

TEST EXAMPLE 30

Flooding treatment test in paddy field

Wager's pots of 200 cm² were filled with paddy field soil, and seeds of barnyardgrass and broadleaf weeds (i.e. false pimpernel, indian toothcup, water wort and red stem [Ammannia spp.]) were sowed 1 to 2 cm deep under the soil surface. After creating the state of paddy field by water flooding, tubers of arrowhead were buried 1 to 2 cm deep under the soil surface. Also rice seedlings of 2-leaf stage were transplanted into the pots. The weeds and crop were cultivated in a greenhouse. After 11 days (at the 2-leaf stage of barnyardgrass), the test compounds were formulated into emulsifiable concentrates according to Formulation Example 2, a prescribed amount of each of the emulsifiable concentrates was diluted with 10 ml of water and applied onto the water surface in the pots. Water leakage deceasing the depth of flooding water by 3 cm was carried out on the day subsequent to and two days after the application of test compounds. The depth of flooding water in each pot was recovered and kept at 4 cm, while the test plants were cultivated for 20 days in a greenhouse. Then, the herbicidal activity and phytotoxicity was examined. The results are shown in Table 33.

TABLE 33

| Test compound | Dosage rate of active ingredient (g/a) | Phytotoxicity Rice | Herbicidal activity | | |
|---|---|---|---|---|---|
| | | | Barnyard grass | Broadleaf weeds | Arrowhead |
| (V-4) | 0.31 | 1 | 5 | 4 | 4 |
| (III-7) | 0.31 | 0 | 4 | 4 | 3 |
| (III-9) | 0.31 | 1 | 4 | 3 | 4 |
| A | 0.31 | 0 | 0 | 0 | 2 |
| J | 0.31 | 0 | 1 | 0 | 0 |

What is claimed is:

1. A pyrimidine compound having the formula:

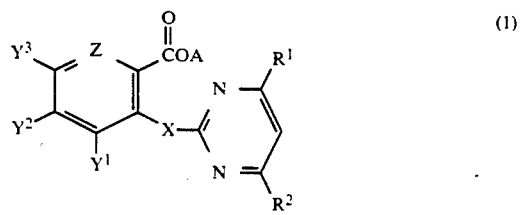

wherein A is 4-7 membered saturated aliphatic hetero ring containing oxygen as the sole hereto atom, 4-7 membered saturated aliphatic hetero ring containing oxygen as the sole hetero atom which ring is further substituted with at least one member selected from the group consisting of $C_1$-$C_6$ alkyl, and halogen, $C_1$-$C_6$ alkyl having a 3-7 membered saturated aliphatic hetero ring containing oxygen as the sole hetero atom, $C_1$-$C_6$ alkyl having a 3-7 membered saturated aliphatic hetero ring containing oxygen as the sole hetero atom which ring is further substituted with at least one member selected from the group consisting of $C_1$-$C_6$ alkyl and halogen, 5∫7 membered saturated aliphatic hetero ring containing as the sole hetero atoms 2 non-adjacent oxygen atoms, 5∫7 membered saturated aliphatic hetero ring containing as the sole hetero atoms 2 non-adjacent oxygen atoms which ring is further substituted with at least one member selected from the group consisting of $C_1$-$C_6$ alkyl and halogen, $C_1$-$C_6$ alkyl having a 5-7 membered saturated aliphatic hetero ring containing as the sole hetero atoms two non-adjacent oxygen atoms or $C_1$-$C_6$ alkyl having a 5-7 membered saturated aliphatic hetero ring containing as the sole hetero atoms two non-adjacent oxygen atoms which ring is further substituted with at least one member selected from the group consisting of $C_1$-$C_6$ alkyl and halogen;
  each of $R^1$ and $R^2$, which may be the same or different, is $C_1$-$C_6$ alkyl, $C_1$-$C_6$ alkoxy, halo $C_1$-$C_6$ alkoxy or halogen;
  X is oxygen or sulfur;
  Z is nitrogen or $CY^4$;
  each of $Y^1$, $Y^2$ and $Y^3$, which may be the same or different, is hydrogen, halogen, $C_1$-$C_6$ alkyl or $C_1$-$C_6$ alkoxy; and
  $Y^4$ is hydrogen, hydroxyl, mercapto, nitro, halogen, $C_1$-$C_6$ alkyl, $C_1$-$C_6$ alkoxy, halo $C_1$-$C_6$ alkyl, halo $C_1$-$C_6$ alkoxy, cyano, formyl, carboxyl, $C_1$-$C_6$ alkoxycarbonyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, $$-N\begin{array}{c}R^5\\ \\ R^6\end{array}$$

wherein each of $R^5$ and $R^6$, which may be the same or different, is hydrogen or $C_1$-$C_6$ alkyl $$-\underset{\underset{O}{\parallel}}{C}-N\begin{array}{c}R^5\\ \\ R^6\end{array}$$

wherein $R^5$ and $R^6$ are as defined above, $$-\underset{(O)_m}{\underset{\parallel}{S}}-R^7,$$

wherein $R^7$ is $C_1$-$C_6$ alkyl and m is an integer of 0, 1 or 2, or $$-X^1-\underset{\underset{O}{\parallel}}{C}-R^7,$$

wherein $X^1$ is oxygen or sulfur, and $R^7$ is as defined above.

2. A pyrimidine compound according to claim 1, wherein A is $C_1$-$C_6$ alkyl having a 5-7 membered saturated aliphatic hetero ring containing as the sole hetero atoms two non-adjacent oxygen atoms.

3. A pyrimidine compound according to claim 2, wherein A is (1,3-dioxolane-2-yl) $C_1$-$C_6$ alkyl or (1,3-dioxan-2-yl) $C_1$-$C_6$ alkyl.

4. A pyrimidine compound according to claim 3, wherein A is (1,3-dioxolane-2-yl)ethyl or (1,3-dioxan-2-yl)ethyl.

5. A pyrimidine compound according to claim 1, wherein each of $R^1$ and $R^2$, which may be the same or different, is $C_1$-$C_6$ alkoxy.

6. A pyrimidine compound according to claim 2, wherein both $R^1$ and $R^2$ are methoxy.

7. A pyrimidine compound according to claim 1, wherein X is oxygen.

8. A pyrimidine compound according to claim 1, wherein Z is nitrogen or $CY^4$ wherein $CY^4$ is hydrogen, halogen, halo $C_1$-$C_6$ alkyl, $C_1$-$C_6$ alkyl, $C_1$-$C_6$ alkoxy, phenyl or phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen.

9. A pyrimidine compound according to claim 3, wherein Z is nitrogen, CH, CF, CCl, CBr or CI.

10. A pyrimidine compound according to claim 5, wherein Z is CF, CCl, CBr or CI.

11. A pyrimidine derivative according to claim 1, wherein both $Y^1$ and $Y^2$ are hydrogen or fluorine, and $Y^3$ is hydrogen, fluorine or $C^1$-$C^6$ alkoxy.

12. A pyrimidine compound according to claim 2, wherein both $R^1$ and $R^2$ are methoxy, and X is oxygen.

13. A pyrimidine compound according to claim 3, wherein both $R^1$ and $R^2$ are methoxy, and X is oxygen.

14. A pyrimidine compound according to claim 4, wherein both $R^1$ and $R^2$ are methoxy, and X is oxygen.

15. A pyrimidine compound according to claim 8, wherein both $R^1$ and $R^2$ are methoxy, and X is oxygen.

16. A herbicidal composition which comprises as an active ingredient a herbicidally effective amount of a pyrmidine compound having the formula, (1)

wherein A is 4-7 membered saturated aliphatic hetero ring containing oxygen as the sole hetero atom, 4-7 membered saturated aliphatic hetero ring containing oxygen as the sole hetero atom which ring is further substituted with at least one member selected from the group consisting of $C_1$-$C_6$ alkyl and halogen, $C_1$-$C_6$ alkyl having a 3-7 membered saturated aliphatic hetero ring containing oxygen as the sole hetero atom, $C_1$-$C_6$ alkyl having a 3-7 membered saturated aliphatic hetero ring containing oxygen as the sole hetero atom which ring is further substituted with at least one member selected from the group consisting of $C_1$-$C_6$ alkyl and halogen, 5-7 membered saturated aliphatic hetero ring containing as the sole hetero atoms 2 non-adjacent oxygen atoms, 5-7 membered saturated aliphatic hetero ring containing as the sole hetero atoms 2 non-adjacent oxygen atoms which ring is further substituted with at least one member selected from the group consisting of $C_1$-$C_6$ alkyl and halogen, $C_1$-$C_6$ alkyl having a 5-7 membered saturated aliphatic hetero ring containing as the sole hetero atoms two non-adjacent oxygen atoms or $C_1$-$C_6$ alkyl having a 5-7 membered saturated aliphatic hetero ring containing as the sole hetero atoms two non-adjacent oxygen atoms which ring is further substituted with at least one member selected from the group consisting of $C_1$-$C_6$ alkyl and halogen;

each of $R^1$ and $R^2$; which may be the same or different, is $C_1$-$C_6$ alkyl, $C_1$-$C_6$ alkoxy, halo $C_1$-$C_6$ alkoxy or halogen;

X is oxygen or sulfur;

Z is nitrogen or $CY^4$;

each of $Y^1$, $Y^2$ and $Y^3$, which may be the same or different, is hydrogen, halogen, $C_1$-$C_6$ alkyl or $C_1$-$C_6$ alkoxy; and $Y^4$ is hydrogen, hydroxyl, mercapto, nitro, halogen, $C_1$-$C_6$ alkyl, $C_1$-$C_6$ alkoxy, halo $C_1$-$C_6$ alkyl, halo $C_1$-$C_6$ alkoxy, cyano, formyl, carboxyl, $C_1$-$C_6$ alkoxycarbonyl, phenyl, phenyl substituted with at least one member selected from the group consisting of $C_1$-$C_6$ alkyl, $C_1$-$C_6$ alkoxy, halo $C_1$-$C_6$ alkyl, $C_1$-$C_6$ alkoxycarbonyl and halogen, $$-N\begin{array}{c}R^5\\ \\ R^6\end{array}$$

wherein each of $R^5$ and $R^6$, which may be the same or different, is hydrogen or $C_1$-$C_6$ alkyl,

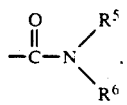

wherein $R^5$ and $R^6$ are as defined above,

wherein $R^7$ is $C_1$–$C_6$ alkyl and m is an integer of 0, 1 or 2, or $$-X^1-\overset{\overset{O}{\|}}{C}-R^7.$$

wherein $X^1$ is oxygen or sulfur, and $R^7$ is as defined above; and an inert carrier or a diluent.

17. A method for controlling undesirable weeds, which comprises applying the herbicidal composition of claim 16 to an area where undesirable weeds grow or are likely to grow.

* * * * *